(12) United States Patent
McMillen

(10) Patent No.: US 10,268,315 B2
(45) Date of Patent: *Apr. 23, 2019

(54) TWO-DIMENSIONAL SENSOR ARRAYS

(71) Applicant: BeBop Sensors, Inc., Berkeley, CA (US)

(72) Inventor: Keith A. McMillen, Berkeley, CA (US)

(73) Assignee: BeBop Sensors, Inc., Berkeley, CA (US)

(*) Notice: Subject to any disclaimer, the term of this patent is extended or adjusted under 35 U.S.C. 154(b) by 32 days.

This patent is subject to a terminal disclaimer.

(21) Appl. No.: 15/483,926

(22) Filed: Apr. 10, 2017

(65) Prior Publication Data

US 2017/0212638 A1     Jul. 27, 2017

Related U.S. Application Data

(63) Continuation of application No. 14/800,538, filed on Jul. 15, 2015, now Pat. No. 9,652,101, which is a (Continued)

(51) Int. Cl.
A61B 5/00 (2006.01)
G01L 1/18 (2006.01)
(Continued)

(52) U.S. Cl.
CPC .......... G06F 3/0418 (2013.01); A43B 3/0005 (2013.01); A61B 5/6807 (2013.01);
(Continued)

(58) Field of Classification Search
CPC ........ G06F 3/044; G06F 3/0416; G06F 3/041; G06F 3/047; G06F 3/045; G06F 3/0412;
(Continued)

(56) References Cited

U.S. PATENT DOCUMENTS 4,294,014 A    10/1981    Baumann et al.
4,438,291 A    3/1984    Eichelberger et al.
(Continued)

FOREIGN PATENT DOCUMENTS

CN    200980381 Y    11/2007
CN    201920728 U    8/2011
(Continued)

OTHER PUBLICATIONS

U.S. Office Action dated Sep. 12, 2012 issued in U.S. Appl. No. 12/904,657.
(Continued)

*Primary Examiner* — Dismery Mercedes
(74) *Attorney, Agent, or Firm* — Weaver Austin Villeneuve & Sampson LLP

(57) ABSTRACT

Sensors incorporating piezoresistive materials are described. One class of sensors includes piezoresistive material that is held or otherwise supported adjacent conductive traces on a substrate. Another class of sensors includes conductive traces formed directly on the piezoresistive material. Two-dimensional sensor arrays incorporating piezoresistive materials are also described.

18 Claims, 21 Drawing Sheets

Related U.S. Application Data continuation of application No. 14/464,551, filed on Aug. 20, 2014, now Pat. No. 9,442,614, which is a continuation-in-part of application No. 14/299,976, filed on Jun. 9, 2014, now Pat. No. 9,965,076.

(60) Provisional application No. 61/993,953, filed on May 15, 2014, provisional application No. 61/993,953, filed on May 15, 2014.

(51) Int. Cl.
| | | |
|---|---|---|
| *G06F 3/041* | (2006.01) | |
| *G06F 3/045* | (2006.01) | |
| *G01L 9/00* | (2006.01) | |
| *G06F 1/16* | (2006.01) | |
| *G01L 9/06* | (2006.01) | |
| *G01L 5/00* | (2006.01) | |
| *G06F 3/044* | (2006.01) | |
| *A43B 3/00* | (2006.01) | |
| *G01L 5/16* | (2006.01) | |
| *A61B 90/00* | (2016.01) | |

(52) U.S. Cl.
CPC .............. *A61B 5/6843* (2013.01); *G01L 1/18* (2013.01); *G01L 5/0019* (2013.01); *G01L 9/0052* (2013.01); *G01L 9/06* (2013.01); *G06F 1/16* (2013.01); *G06F 3/044* (2013.01); *G06F 3/045* (2013.01); *G06F 3/0414* (2013.01); *G06F 3/0416* (2013.01); *A61B 5/6804* (2013.01); *A61B 2090/064* (2016.02); *A61B 2562/0247* (2013.01); *A61B 2562/046* (2013.01); *G01L 5/16* (2013.01); *G06F 2203/04102* (2013.01); *G06F 2203/04103* (2013.01); *G06F 2203/04104* (2013.01); *G06F 2203/04112* (2013.01)

(58) Field of Classification Search
CPC ......... G06F 3/0414; G06F 2203/04103; G06F 2203/04104; G06F 2203/04111; G06F 2203/04102; G06F 2203/04106; G06F 2203/04112; G06F 1/16; G01L 1/18; G01L 1/205; G01L 1/146; G01L 9/0052; G01L 9/06; G01L 1/20; G01L 5/228; G01L 5/0019; G01L 5/0038; G01L 5/0052; A61B 2562/0247; A61B 2562/046; A61B 5/6843; A61B 5/6807; A61B 5/6806; A61B 5/6804; A61B 2090/064
See application file for complete search history.

(56) References Cited

U.S. PATENT DOCUMENTS

| | | |
|---|---|---|
| 4,489,302 A | 12/1984 | Eventoff |
| 4,693,530 A | 9/1987 | Stillie et al. |
| 4,745,301 A | 5/1988 | Michalchik |
| 4,790,968 A * | 12/1988 | Ohkawa .............. H01C 10/106 200/264 |
| 4,852,443 A | 8/1989 | Duncan et al. |
| 5,033,291 A | 7/1991 | Podoloff et al. |
| 5,128,880 A | 7/1992 | White |
| 5,131,306 A | 7/1992 | Yamamoto |
| 5,159,159 A * | 10/1992 | Asher .................... G01L 1/205 178/18.05 |
| 5,219,292 A | 6/1993 | Dickirson et al. |
| 5,237,520 A | 8/1993 | White |
| 5,288,938 A | 2/1994 | Wheaton |
| 5,316,017 A | 5/1994 | Edwards et al. |
| 5,429,092 A | 7/1995 | Kamei |
| 5,571,973 A | 11/1996 | Taylot |
| 5,578,766 A | 11/1996 | Kondo |
| 5,624,132 A | 4/1997 | Blackburn et al. |
| 5,659,395 A | 8/1997 | Brown et al. |
| 5,695,859 A | 12/1997 | Burgess |
| 5,729,905 A | 3/1998 | Mathiasmeier et al. |
| 5,822,223 A | 10/1998 | Genest |
| 5,866,829 A | 2/1999 | Pecoraro |
| 5,878,359 A | 3/1999 | Takeda |
| 5,943,044 A | 8/1999 | Martinelli et al. |
| 5,989,700 A | 11/1999 | Krivopal |
| 6,029,358 A | 2/2000 | Mathiasmeier et al. |
| 6,032,109 A | 2/2000 | Ritmiller, III |
| 6,049,327 A | 4/2000 | Walker et al. |
| 6,087,930 A | 7/2000 | Kulka et al. |
| 6,121,869 A | 9/2000 | Burgess |
| 6,141,643 A | 10/2000 | Harmon |
| 6,155,120 A * | 12/2000 | Taylor .................. A61B 5/1036 73/862.046 |
| 6,215,055 B1 | 4/2001 | Saravis |
| 6,216,545 B1 | 4/2001 | Taylor |
| 6,304,840 B1 | 10/2001 | Vance et al. |
| 6,331,893 B1 | 12/2001 | Brown et al. |
| 6,360,615 B1 | 3/2002 | Smela |
| 6,452,479 B1 * | 9/2002 | Sandbach ............... G06F 3/045 338/101 |
| 6,486,776 B1 | 11/2002 | Pollack et al. |
| 6,687,523 B1 | 2/2004 | Jayaramen et al. |
| 6,763,320 B2 | 7/2004 | Kimble |
| 6,815,602 B2 | 11/2004 | De Franco |
| 6,822,635 B2 | 11/2004 | Shahoian et al. |
| 6,829,942 B2 | 12/2004 | Yanai et al. |
| 6,964,205 B2 | 11/2005 | Papakostas et al. |
| 7,037,268 B1 | 5/2006 | Sleva et al. |
| 7,066,887 B2 | 6/2006 | Flesch et al. |
| 7,109,068 B2 | 9/2006 | Akram et al. |
| 7,113,856 B2 | 9/2006 | Theiss et al. |
| 7,157,640 B2 | 1/2007 | Baggs |
| 7,302,866 B1 | 12/2007 | Malkin et al. |
| 7,311,009 B2 | 12/2007 | Kotovsky |
| 7,332,670 B2 | 2/2008 | Fujiwara et al. |
| 7,409,256 B2 | 8/2008 | Lin et al. |
| 7,439,465 B2 | 10/2008 | Parkinson |
| 7,493,230 B2 | 2/2009 | Schwartz et al. |
| 7,536,794 B2 | 5/2009 | Hay et al. |
| 7,608,776 B2 | 10/2009 | Ludwig |
| 7,719,007 B2 | 5/2010 | Tompkins et al. |
| 7,754,956 B2 | 7/2010 | Gain et al. |
| 7,780,541 B2 | 8/2010 | Bauer |
| 7,855,718 B2 | 12/2010 | Westerman |
| 7,928,312 B2 | 4/2011 | Sharma |
| 7,984,544 B2 | 7/2011 | Rosenberg |
| 8,109,149 B2 | 2/2012 | Kotovsky |
| 8,117,922 B2 | 2/2012 | Xia et al. |
| 8,120,232 B2 | 2/2012 | Daniel et al. |
| 8,127,623 B2 | 3/2012 | Son et al. |
| 8,161,826 B1 | 4/2012 | Taylor |
| 8,250,934 B2 | 8/2012 | Sakurai |
| 8,274,485 B2 | 9/2012 | Liu et al. |
| 8,346,684 B2 | 1/2013 | Mirbach et al. |
| 8,368,505 B2 * | 2/2013 | Deppiesse ............ H03K 17/965 338/114 |
| 8,448,530 B2 | 5/2013 | Leuenberger et al. |
| 8,479,585 B2 | 7/2013 | Shaw-Klein |
| 8,536,880 B2 | 9/2013 | Philipp |
| 8,571,827 B2 | 10/2013 | Jang et al. |
| 8,680,390 B2 | 3/2014 | McMillen et al. |
| 8,813,579 B2 | 8/2014 | Aufrere |
| 8,857,274 B2 | 10/2014 | Mamigonians |
| 8,884,913 B2 | 11/2014 | Saynac et al. |
| 8,892,051 B2 | 11/2014 | Yi et al. |
| 8,904,876 B2 | 12/2014 | Taylor et al. |
| 8,925,392 B2 | 1/2015 | Esposito et al. |
| 8,925,393 B2 | 1/2015 | Cannard et al. |
| 8,945,328 B2 | 2/2015 | Longinotti-Buitoni et al. |
| 8,947,889 B2 | 2/2015 | Kelley et al. |
| 8,950,265 B2 * | 2/2015 | Dunn .................... G01L 9/0072 73/714 |
| 8,964,205 B2 | 2/2015 | Shimizu |
| 8,970,513 B2 | 3/2015 | Kwon et al. |

(56) References Cited

U.S. PATENT DOCUMENTS

| | | | |
|---|---|---|---|
| 9,032,804 B2* | 5/2015 | Granado | G01L 9/0052 73/700 |
| 9,038,482 B2 | 5/2015 | Xia et al. | |
| 9,075,404 B2 | 7/2015 | McMillen et al. | |
| 9,076,419 B2 | 7/2015 | McMillen et al. | |
| 9,112,058 B2 | 8/2015 | Bao et al. | |
| 9,116,569 B2* | 8/2015 | Stacy | G06F 3/016 |
| 9,164,586 B2 | 10/2015 | Zellers et al. | |
| 9,271,665 B2 | 3/2016 | Sarrafzadeh et al. | |
| 9,417,693 B2 | 8/2016 | Seth | |
| 9,442,614 B2 | 9/2016 | McMillen | |
| 9,480,582 B2 | 11/2016 | Lundborg | |
| 9,529,433 B2 | 12/2016 | Shankar et al. | |
| 9,546,921 B2 | 1/2017 | McMillen et al. | |
| 9,652,101 B2 | 5/2017 | McMillen et al. | |
| 9,682,856 B2 | 6/2017 | Whitesides et al. | |
| 9,696,833 B2 | 7/2017 | McMillen | |
| 9,710,060 B2* | 7/2017 | McMillen | H03K 17/964 |
| 9,721,553 B2 | 8/2017 | McMillen et al. | |
| 9,753,568 B2 | 9/2017 | McMillen | |
| 9,827,996 B2* | 11/2017 | McMillen | B60W 50/0098 |
| 9,836,151 B2 | 12/2017 | McMillen | |
| 9,863,823 B2 | 1/2018 | McMillen | |
| 9,965,076 B2 | 5/2018 | McMillen | |
| 10,082,381 B2 | 9/2018 | McMillen et al. | |
| 2002/0078757 A1 | 6/2002 | Hines et al. | |
| 2002/0180578 A1 | 12/2002 | Sandbach | |
| 2004/0031180 A1 | 2/2004 | Ivanov | |
| 2004/0093746 A1 | 5/2004 | Varsallona | |
| 2004/0183648 A1 | 9/2004 | Weber et al. | |
| 2004/0189145 A1 | 9/2004 | Pletner et al. | |
| 2004/0252007 A1* | 12/2004 | Lussey | H01H 3/141 338/47 |
| 2005/0109095 A1 | 5/2005 | Sinnett | |
| 2005/0220673 A1 | 10/2005 | Thaysen | |
| 2007/0063992 A1 | 3/2007 | Lundquist | |
| 2007/0129776 A1 | 6/2007 | Robins et al. | |
| 2007/0151348 A1 | 7/2007 | Zdeblick et al. | |
| 2007/0188179 A1 | 8/2007 | Deangelis et al. | |
| 2007/0188180 A1* | 8/2007 | Deangelis | G01D 5/2405 324/661 |
| 2007/0202765 A1 | 8/2007 | Krans et al. | |
| 2007/0234888 A1 | 10/2007 | Rotolo de Moraes | |
| 2008/0069412 A1 | 3/2008 | Champagne et al. | |
| 2008/0158145 A1 | 7/2008 | Westerman | |
| 2008/0189827 A1 | 8/2008 | Bauer | |
| 2008/0254824 A1 | 10/2008 | Rotolo de Moraes | |
| 2009/0013793 A1 | 1/2009 | Kim et al. | |
| 2009/0049980 A1 | 2/2009 | Sharma | |
| 2009/0237374 A1 | 9/2009 | Li et al. | |
| 2009/0272197 A1 | 11/2009 | Ridao Granado et al. | |
| 2009/0301190 A1 | 12/2009 | Ross, Jr. et al. | |
| 2009/0303400 A1 | 12/2009 | Hou et al. | |
| 2010/0066572 A1 | 3/2010 | Dietz et al. | |
| 2010/0123686 A1 | 5/2010 | Klinghult et al. | |
| 2010/0134327 A1 | 6/2010 | Dinh et al. | |
| 2010/0149108 A1 | 6/2010 | Hotelling et al. | |
| 2010/0179724 A1 | 7/2010 | Weston | |
| 2010/0199777 A1 | 8/2010 | Hooper et al. | |
| 2010/0242274 A1 | 9/2010 | Rosenfeld et al. | |
| 2010/0274447 A1 | 10/2010 | Stumpf | |
| 2010/0286951 A1 | 11/2010 | Danenberg et al. | |
| 2010/0292945 A1 | 11/2010 | Reynolds et al. | |
| 2010/0315337 A1 | 12/2010 | Ferren et al. | |
| 2011/0005090 A1* | 1/2011 | Lee | G01D 5/145 33/1 PT |
| 2011/0088535 A1 | 4/2011 | Zarimis | |
| 2011/0088536 A1* | 4/2011 | McMillen | G10H 1/348 84/746 |
| 2011/0107771 A1 | 5/2011 | Crist et al. | |
| 2011/0141052 A1 | 6/2011 | Bernstein et al. | |
| 2011/0153261 A1 | 6/2011 | Jang et al. | |
| 2011/0199284 A1 | 8/2011 | Davis et al. | |
| 2011/0221564 A1 | 9/2011 | Deppiesse et al. | |
| 2011/0241850 A1 | 10/2011 | Bosch et al. | |
| 2011/0246028 A1 | 10/2011 | Lisseman et al. | |
| 2011/0260994 A1 | 10/2011 | Saynac et al. | |
| 2011/0271772 A1 | 11/2011 | Parks et al. | |
| 2011/0279409 A1 | 11/2011 | Salaverry et al. | |
| 2011/0302694 A1 | 12/2011 | Wang et al. | |
| 2012/0007831 A1 | 1/2012 | Chang et al. | |
| 2012/0024132 A1 | 2/2012 | Wallace et al. | |
| 2012/0026124 A1 | 2/2012 | Li et al. | |
| 2012/0055257 A1 | 3/2012 | Shaw-Klein | |
| 2012/0090408 A1* | 4/2012 | Jheng | G01L 1/18 73/862.68 |
| 2012/0143092 A1 | 6/2012 | Xia et al. | |
| 2012/0191554 A1 | 7/2012 | Xia et al. | |
| 2012/0197161 A1 | 8/2012 | Xia et al. | |
| 2012/0198949 A1 | 8/2012 | Xia et al. | |
| 2012/0222498 A1* | 9/2012 | Mamigonians | G01L 1/142 73/862.626 |
| 2012/0234105 A1 | 9/2012 | Taylor | |
| 2012/0283979 A1 | 11/2012 | Bruekers et al. | |
| 2012/0296528 A1 | 11/2012 | Wellhoefer et al. | |
| 2012/0297885 A1 | 11/2012 | Hou et al. | |
| 2012/0299127 A1 | 11/2012 | Fujii et al. | |
| 2012/0312102 A1 | 12/2012 | Alvarez et al. | |
| 2012/0323501 A1 | 12/2012 | Sarrafzadeh et al. | |
| 2013/0009905 A1 | 1/2013 | Castillo et al. | |
| 2013/0055482 A1 | 3/2013 | D'Aprile et al. | |
| 2013/0082970 A1 | 4/2013 | Frey et al. | |
| 2013/0085394 A1 | 4/2013 | Corbett, III et al. | |
| 2013/0113057 A1 | 5/2013 | Taylor | |
| 2013/0165809 A1 | 6/2013 | Abir | |
| 2013/0192071 A1 | 8/2013 | Esposito et al. | |
| 2013/0203201 A1 | 8/2013 | Britton et al. | |
| 2013/0211208 A1 | 8/2013 | Varadan et al. | |
| 2013/0239787 A1* | 9/2013 | McMillen | G10H 1/02 84/643 |
| 2013/0274985 A1 | 10/2013 | Lee et al. | |
| 2013/0275057 A1 | 10/2013 | Perlin et al. | |
| 2013/0327560 A1* | 12/2013 | Ichiki | G06F 3/044 174/133 R |
| 2014/0007704 A1 | 1/2014 | Granado et al. | |
| 2014/0007706 A1 | 1/2014 | Aufrere et al. | |
| 2014/0013865 A1* | 1/2014 | White | G01L 1/14 73/862.626 |
| 2014/0026678 A1 | 1/2014 | Cannard et al. | |
| 2014/0033829 A1 | 2/2014 | Xia et al. | |
| 2014/0090488 A1* | 4/2014 | Taylor | G01L 1/18 73/862.625 |
| 2014/0104776 A1 | 4/2014 | Clayton et al. | |
| 2014/0107966 A1 | 4/2014 | Xia et al. | |
| 2014/0107967 A1 | 4/2014 | Xia et al. | |
| 2014/0107968 A1 | 4/2014 | Xia et al. | |
| 2014/0125124 A1 | 5/2014 | Verner | |
| 2014/0130593 A1* | 5/2014 | Ciou | A61B 5/1038 73/172 |
| 2014/0150573 A1 | 6/2014 | Cannard et al. | |
| 2014/0182170 A1 | 7/2014 | Wawrousek et al. | |
| 2014/0195023 A1 | 7/2014 | Statham et al. | |
| 2014/0215684 A1 | 8/2014 | Hardy et al. | |
| 2014/0222173 A1* | 8/2014 | Giedwoyn | A43B 3/0005 700/91 |
| 2014/0222243 A1 | 8/2014 | McMillen et al. | |
| 2014/0318699 A1 | 10/2014 | Longinotti-Buitoni et al. | |
| 2014/0347076 A1 | 11/2014 | Barton et al. | |
| 2015/0035743 A1 | 2/2015 | Rosener | |
| 2015/0084873 A1 | 3/2015 | Hagenbuch et al. | |
| 2015/0086955 A1 | 3/2015 | Poniatowski et al. | |
| 2015/0130698 A1 | 5/2015 | Burgess | |
| 2015/0168238 A1 | 6/2015 | Raut et al. | |
| 2015/0177080 A1 | 6/2015 | Esposito et al. | |
| 2015/0248159 A1 | 9/2015 | Luo et al. | |
| 2015/0261372 A1 | 9/2015 | McMillen et al. | |
| 2015/0316434 A1 | 11/2015 | McMillen et al. | |
| 2015/0317964 A1 | 11/2015 | McMillen et al. | |
| 2015/0330855 A1 | 11/2015 | Daniecki et al. | |
| 2015/0331512 A1 | 11/2015 | McMillen et al. | |
| 2015/0331522 A1 | 11/2015 | McMillen et al. | |

(56) References Cited

U.S. PATENT DOCUMENTS

| | | | |
|---|---|---|---|
| 2015/0331523 A1 | 11/2015 | McMillen et al. | |
| 2015/0331524 A1 | 11/2015 | McMillen et al. | |
| 2015/0331533 A1 | 11/2015 | McMillen et al. | |
| 2015/0370396 A1 | 12/2015 | Hotelling et al. | |
| 2016/0052131 A1 | 2/2016 | Lessing et al. | |
| 2016/0054798 A1 | 2/2016 | Messingher et al. | |
| 2016/0070347 A1 | 3/2016 | McMillen et al. | |
| 2016/0147352 A1 | 5/2016 | Filiz et al. | |
| 2016/0162022 A1 | 6/2016 | Seth | |
| 2016/0169754 A1 | 6/2016 | Kowalewski et al. | |
| 2016/0175186 A1 | 6/2016 | Shadduck | |
| 2016/0187973 A1 | 6/2016 | Shankar et al. | |
| 2016/0209441 A1* | 7/2016 | Mazzeo | G01P 15/125 |
| 2016/0238547 A1 | 8/2016 | Park et al. | |
| 2016/0246369 A1 | 8/2016 | Osman | |
| 2016/0252412 A1 | 9/2016 | McMillen et al. | |
| 2016/0270727 A1 | 9/2016 | Berg et al. | |
| 2016/0278709 A1 | 9/2016 | Granado et al. | |
| 2016/0313798 A1 | 10/2016 | Connor | |
| 2016/0318356 A1 | 11/2016 | McMillen et al. | |
| 2016/0375910 A1 | 12/2016 | McMillen et al. | |
| 2017/0000369 A1 | 1/2017 | Hyde et al. | |
| 2017/0038881 A1 | 2/2017 | McMillen | |
| 2017/0056644 A1 | 3/2017 | Chahine et al. | |
| 2017/0086519 A1 | 3/2017 | Vigano et al. | |
| 2017/0110103 A1 | 4/2017 | McMillen et al. | |
| 2017/0127736 A1 | 5/2017 | Roberts et al. | |
| 2017/0167931 A1 | 6/2017 | McMillen et al. | |
| 2017/0303853 A1 | 10/2017 | McMillen et al. | |
| 2017/0305301 A1 | 10/2017 | McMillen et al. | |
| 2018/0015932 A1 | 1/2018 | McMillen et al. | |
| 2018/0094991 A1 | 4/2018 | McMillen et al. | |
| 2018/0263563 A1 | 9/2018 | McMillen et al. | |

FOREIGN PATENT DOCUMENTS

| | | |
|---|---|---|
| CN | 102551728 A | 7/2012 |
| CN | 202396601 U | 8/2012 |
| CN | 203234132 U | 10/2013 |
| CN | 102406280 B | 3/2014 |
| DE | 102 12 023 A1 | 10/2003 |
| DE | 11 2010 004 038 T5 | 9/2012 |
| EP | 0 014 022 B1 | 11/1984 |
| EP | 2 682 724 A1 | 1/2014 |
| JP | H08-194481 A | 7/1996 |
| JP | 2000-267664 A | 9/2000 |
| JP | 2008-515008 A | 5/2008 |
| KR | 10-2007-0008500 A | 1/2007 |
| KR | 100865148 B1 | 10/2008 |
| KR | 10-1362742 B1 | 2/2014 |
| KR | 10-2014-0071693 A | 6/2014 |
| NL | 8900820 A | 11/1990 |
| RU | 2 533 539 C1 | 11/2014 |
| WO | WO 99/020179 A1 | 4/1999 |
| WO | WO 2007/024875 A2 | 3/2007 |
| WO | WO 2009/155891 A1 | 12/2009 |
| WO | WO 2011/047171 A2 | 4/2011 |
| WO | WO 2015/175317 A1 | 11/2015 |
| WO | WO 2016/070078 A1 | 5/2016 |
| WO | WO 2016/138234 A1 | 9/2016 |
| WO | WO 2016/176307 A1 | 11/2016 |
| WO | WO 2016/210173 A1 | 12/2016 |
| WO | WO 2017/066096 A1 | 4/2017 |
| WO | WO 2017/184367 A1 | 10/2017 |

OTHER PUBLICATIONS

U.S. Office Action dated Apr. 15, 2013 issued in U.S. Appl. No. 12/904,657.
U.S. Notice of Allowance dated Nov. 8, 2013 issued in U.S. Appl. No. 12/904,657.
U.S. Office Action dated Mar. 12, 2015 issued in U.S. Appl. No. 14/173,617.
U.S. Notice of Allowance dated May 1, 2015 issued in U.S. Appl. No. 14/173,617.
U.S. Office Action dated Mar. 10, 2016 issued in U.S. Appl. No. 14/727,619.
U.S. Final Office Action dated Jul. 18, 2016 issued in U.S. Appl. No. 14/727,619.
U.S. Notice of Allowance dated Sep. 15, 2016 issued in U.S. Appl. No. 14/727,619.
U.S. Office Action dated Apr. 2, 2015 issued in U.S. Appl. No. 13/799,304.
U.S. Notice of Allowance dated Apr. 24, 2015 issued in U.S. Appl. No. 13/799,304.
U.S. Office Action dated Sep. 1, 2015 issued in U.S. Appl. No. 14/728,872.
U.S. Final Office Action dated Mar. 9, 2016 issued in U.S. Appl. No. 14/728,872.
U.S. Office Action dated Jun. 22, 2016 issued in U.S. Appl. No. 14/728,872.
U.S. Final Office Action dated Oct. 18, 2016 issued in U.S. Appl. No. 14/728,872.
U.S. Advisory Action dated Feb. 10, 2017 issued in U.S. Appl. No. 14/728,872.
U.S. Office Action dated Jul. 25, 2016 issued in U.S. Appl. No. 14/728,873.
U.S. Office Action dated Dec. 30, 2016 issued in U.S. Appl. No. 14/728,873.
U.S. Office Action dated Mar. 9, 2016 issued in U.S. Appl. No. 14/299,976.
U.S. Final Office Action dated Jul. 6, 2016 issued in U.S. Appl. No. 14/299,976.
U.S. Office Action dated Oct. 21, 2016 issued in U.S. Appl. No. 14/299,976.
U.S. Office Action dated Jan. 13, 2016 issued in U.S. Appl. No. 14/464,551.
U.S. Notice of Allowance dated Jun. 23, 2016 issued in U.S. Appl. No. 14/464,551.
U.S. Office Action dated Sep. 23, 2016 issued in U.S. Appl. No. 14/800,538.
U.S. Notice of Allowance dated Jan. 17, 2017 issued in U.S. Appl. No. 14/800,538.
U.S. Office Action dated Feb. 22, 2017 issued in U.S. Appl. No. 14/671,821.
U.S. Office Action dated Jun. 28, 2016 issued in U.S. Appl. No. 14/671,844.
U.S. Final Office Action dated Nov. 25, 2016 issued in U.S. Appl. No. 14/671,844.
U.S.Notice of Allowance dated Mar. 13, 2017 issued in U.S. Appl. No. 14/671,844.
U.S. Office Action dated Jan. 26, 2017 issued in U.S. Appl. No. 15/052,293.
U.S. Office Action dated May 20, 2016 issued in U.S. Appl. No. 14/928,058.
U.S. Final Office Action dated Jan. 6, 2017 issued in U.S. Appl. No. 14/928,058.
U.S. Notice of Allowance dated Mar. 16, 2017 issued in U.S. Appl. No. 14/928,058.
PCT International Search Report dated May 27, 2011, issued in PCT/US2010/052701.
PCT International Preliminary Report on Patentability and Written Opinion dated Apr. 26, 2012, issued in PCT/US2010/052701.
Japanese Office Action dated Feb. 25, 2014 issued in JP 2012-534361.
PCT International Search Report and Written Opinion dated Sep. 3, 2015 issued in PCT/US2015/029732.
PCT International Preliminary Report on Patentability and Written Opinion dated Nov. 24, 2016 issued in PCT/US2015/029732.
PCT International Search Report and Written Opinion dated May 26, 2016 issued in PCT/US2016/019513.
PCT International Search Report and Written Opinion dated Apr. 14, 2016 issued in PCT/US2015/058370.
PCT International Search Report and Written Opinion dated Sep. 15, 2016 issued in PCT/US2016/029528.

(56) References Cited

OTHER PUBLICATIONS

PCT International Search Report and Written Opinion dated Sep. 29, 2016 issued in PCT/US2016/039089.
PCT International Search Report and Written Opinion dated Jan. 19, 2017 issued in PCT/US2016/055997.
"Electronic Foot Size Measuring Devices," *Sensatech Research LTD., Custom Electronic Sensing Solutions*, Registered Office: 4 Heath Square, Boltro Road, Haywards Heath, RH16 1BL Company Registration No. 4524018 Cardiff [retrieved at http:www.electronicsarena.co.uk/companies/sensatech-research/products/electronic-foot-size-measureing-devices on Sep. 17, 2015], 3 pages.
"iStep® Digital Foot Scan," (©2002-2015) [retrieved at http://www.foot.com/site/iStep on Sep. 17, 2015], 1 page.
"Podotech Elftman," and Podotech Elftman Brochure (UK Version) [retrieved at http://www.podotech.com/diagnostics/podotech-elftman-2/ on Sep. 17, 2015] podo+tech®, Foot Care Technology Solutions, 7 pages.
Roh, Jung-Sim et al. (2011) "Robust and reliable fabric and piezoresistive multitouch sensing surfaces for musical controllers," from Alexander Refsum Jensenius, Recorded at: *11th International Conference on New Interfaces for Musical Expression* May 30-Jun. 1, 2011, Oslo, Norway, a vimeo download at http://vimeo.com/26906580.
"The Emed®-Systems," [retrieved at http://www.novel.de/novelcontent/emed on Sep. 17, 2015] *novel.de*, 4 pages.
U.S. Appl. No. 15/287,520, filed Oct. 6, 2016, McMillen et al.
U.S. Appl. No. 15/374,816, filed Dec. 9, 2016, McMillen et al.
U.S. Office Action dated Dec. 27, 2016 issued in U.S. Appl. No. 15/287,520.
U.S. Notice of Allowance dated Mar. 27, 2017 issued in U.S. Appl. No. 15/287,520.
U.S. Final Office Action dated Mar. 31, 2017 issued in U.S. Appl. No. 14/728,873.
U.S. Final Office Action dated Apr. 19, 2017 issued in U.S. Appl. No. 14/299,976.
U.S. Final Office Action dated May 2, 2017 issued in U.S. Appl. No. 15/052,293.
PCT International Preliminary Report on Patentability and Written Opinion dated May 11, 2017 issued in PCT/US2015/058370.
U.S. Appl. No 15/479,103, filed Apr. 4, 2017, McMillen et al.
U.S. Office Action dated May 19, 2017 issued in U.S. Appl. No. 14/728,872.
U.S. Notice of Allowance dated Oct. 16, 2017 issued in U.S. Appl. No. 14/728,872.
U.S. Advisory Action and Examiner initiated interview summary dated May 26, 2017 issued U.S. Appl. No. 14/728,873.
U.S. Office Action dated Aug. 25, 2017 issued in U.S. Appl. No. 14/728,873.
U.S. Final Office Action dated Dec. 22, 2017 issued in U.S. Appl. No. 14/728,873.
U.S. Office Action dated Mar. 26, 2018 issued in U.S. Appl. No. 14/728,873.
U.S. Notice of Allowance dated Jul. 19, 2018 issued in U.S. Appl. No. 14/728,873.
U.S. Final Office Action dated Jun. 8, 2017 issued in U.S. Appl. No. 14/299,976.
U.S. Office Action dated Sep. 1, 2017 issued in U.S. Appl. No. 14/299,976.
U.S. Notice of Allowance dated Feb. 22, 2018 issued in U.S. Appl. No. 14/299,976.
U.S. Notice of Allowance dated Jul. 3, 2017 issued in U.S. Appl. No. 14/671,821.
U.S. Office Action dated Jun. 30, 2017 issued in U.S. Appl. No. 15/251,772.
U.S. Final Office Action dated Nov. 15, 2017 issued in U.S. Appl. No. 15/251,772.
U.S. Office Action dated Feb. 22, 2018 issued in U.S. Appl. No. 15/251,772.
U.S. Office Action dated Sep. 4, 2018 issued in U.S. Appl. No. 15/251,772.
U.S. Notice of Allowance dated May 24, 2017 issued in U.S. Appl. No. 15/052,293.
U.S. Notice of Allowance [Supplemental Notice of Allowability] dated Jun. 20, 2017 issued in U.S. Appl. No. 15/052,293.
U.S. Notice of Allowance dated Sep. 22, 2017 issued in U.S. Appl. No. 15/052,293.
U.S. Notice of Allowance [Supplemental Notice of Allowability] dated Oct. 19, 2017 issued in U.S. Appl. No. 15/052,293.
U.S. Office Action dated Jul. 24, 2018 issued in U.S. Appl. No. 15/835,131.
U.S. Office Action dated Aug. 14, 2018 issued in U.S. Appl. No. 15/621,935.
U.S. Office Action dated Nov. 3, 2017 issued in U.S. Appl. No. 15/138,802.
U.S. Final Office Action dated Mar. 1, 2018 issued in U.S. Appl. No. 15/138,802.
U.S. Advisory Action dated May 16, 2018 issued in U.S. Appl. No. 15/138,802.
U.S. Notice of Allowance dated Jul. 3, 2018 issued in U.S. Appl. No. 15/138,802.
U.S. Office Action dated Jun. 23, 2017 issued in U.S. Appl. No. 15/190,089.
U.S. Notice of Allowance dated Aug. 10, 2017 issued in U.S. Appl. No. 15/190,089.
PCT International Preliminary Report on Patentability and Written Opinion dated Sep. 8, 2017 issued in PCT/US2016/019513.
PCT International Preliminary Report on Patentability and Written Opinion dated Oct. 31, 2017 issued in PCT/US2016/029528.
PCT International Preliminary Report on Patentability and Written Opinion dated Dec. 26, 2017 issued in PCT/US2016/039089.
PCT International Preliminary Report on Patentability and Written Opinion dated Apr. 26, 2018 issued in PCT/US2016/055997.
PCT International Search Report and Written Opinion dated Aug. 14, 2017 issued in PCT/US2017/026812.
U.S. Appl. No. 15/630,840, filed Jun. 22, 2017, McMillen et al.
U.S. Appl. No. 16/148,570, filed Oct. 1, 2018, McMillen et al.

\* cited by examiner

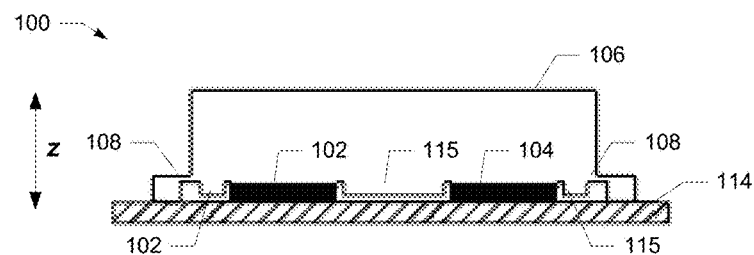
FIG. 1A
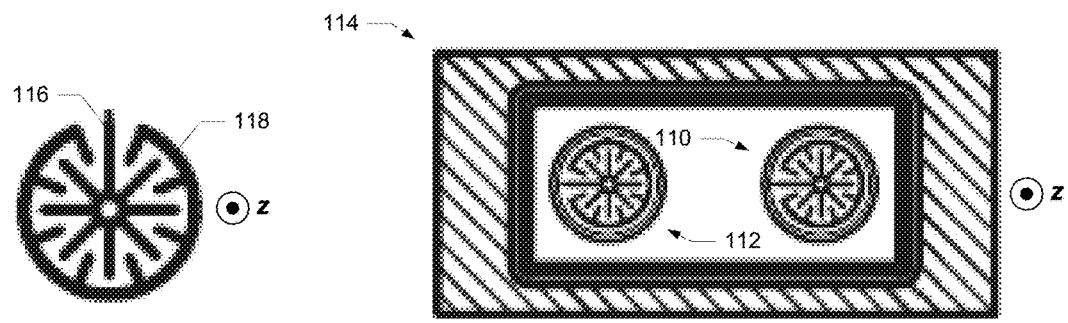
FIG. 1B          FIG. 1C
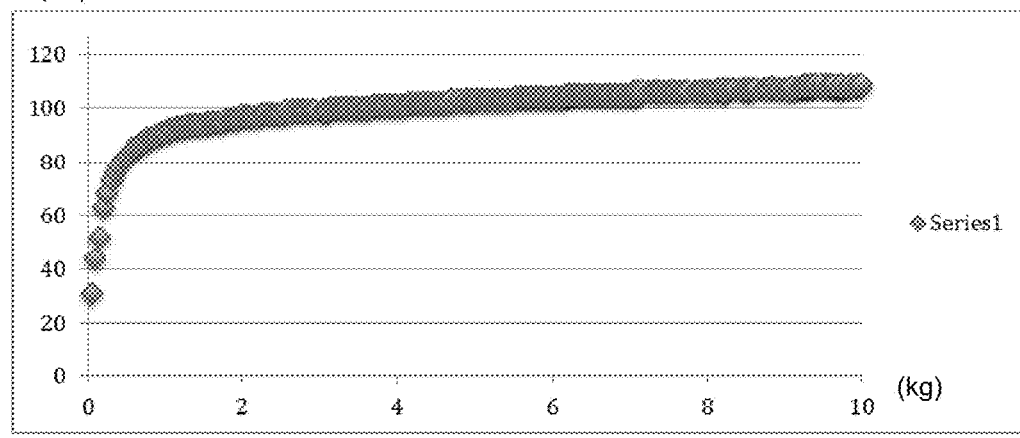
FIG. 1D

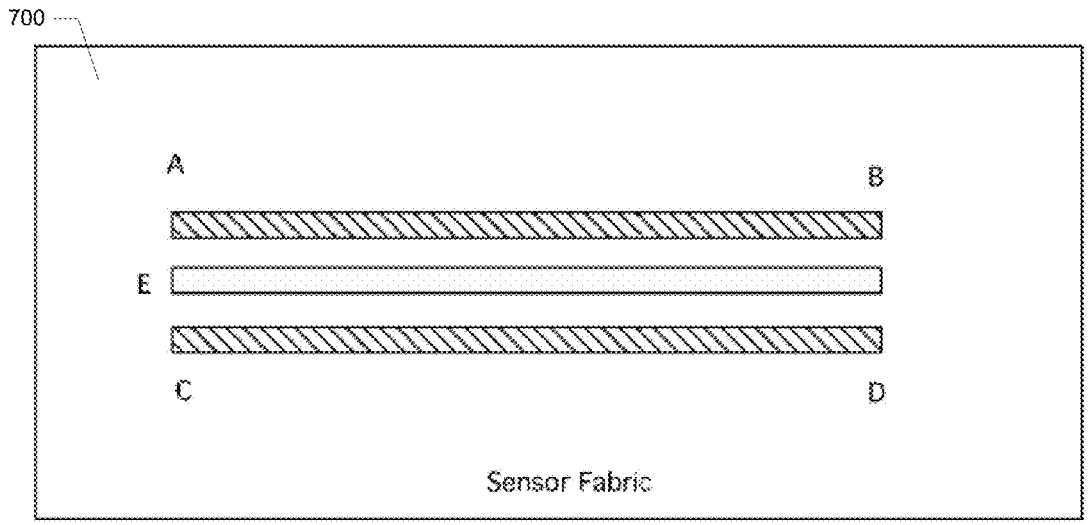

Unique electrical signal sent into points A, B, C, D succesively or sumultaneously. Conductors AB and CD are approx 10% of relaxed surface resistance of Sensor fabric.

Conductor E has near zero resistance andmeasures each of the signals based on increasing pressure to sensor material between elements which reduces resistance causing larger signals of A, B, C, D to be seen on E.

Using ratios of A - B and total Amplitude of A+B position and pressure can be determined.

Measuring ratios of above between signals A-B and C-D location of pressure can be determined between.

If wide contact point or multiple contact points appear along the conductors, a conductive plane behind sensor fabric will allow measurement of signals passed through the fabric to remove ambiguity.

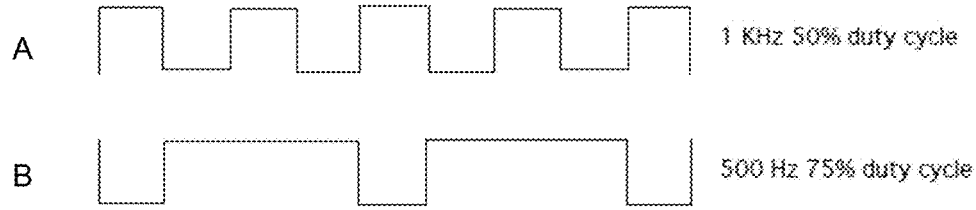

*FIG. 7*

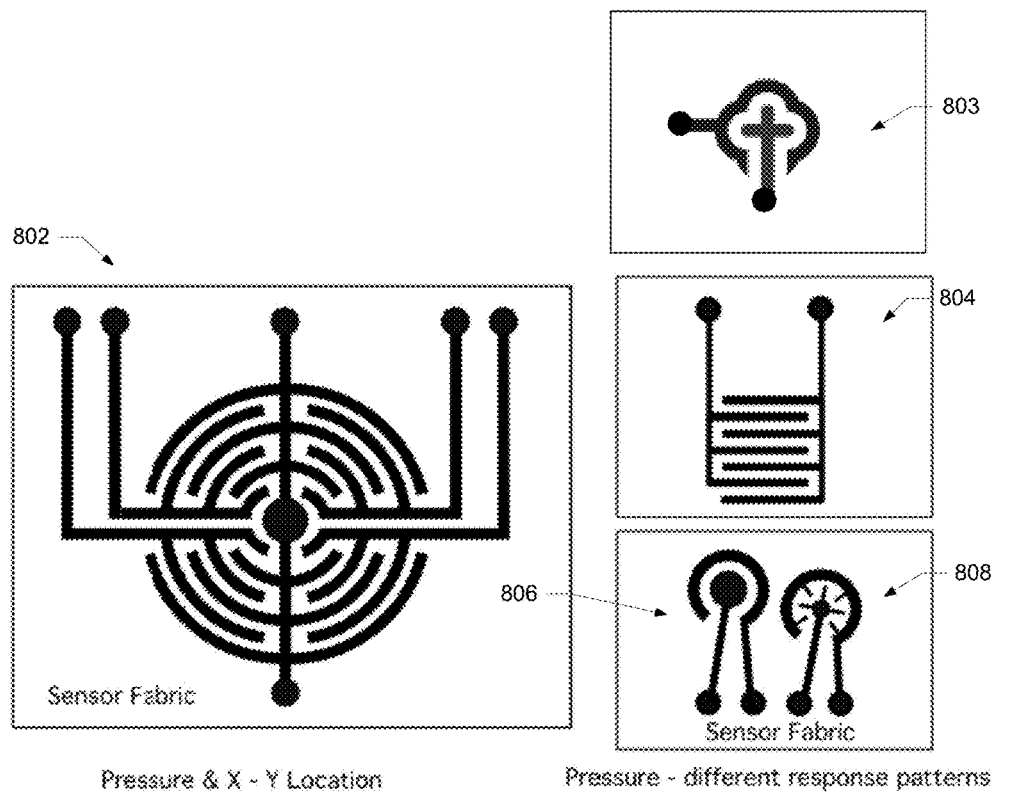
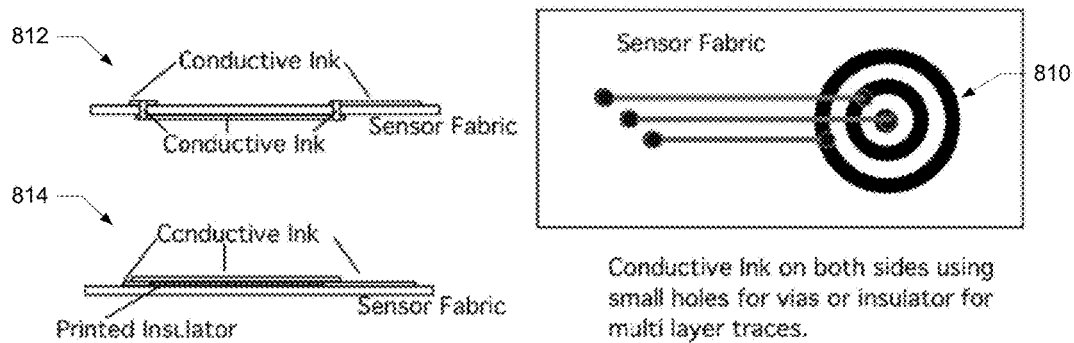
*FIG. 8*

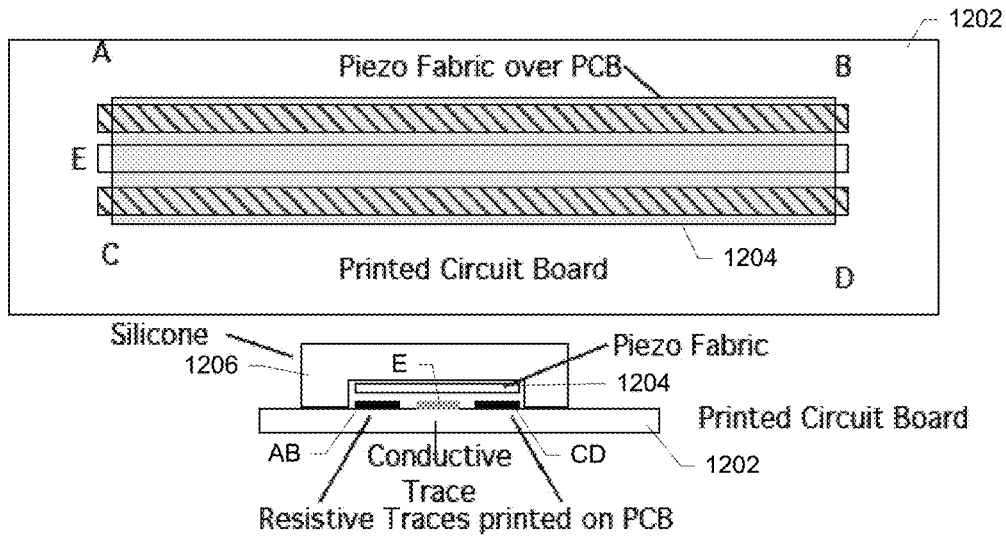

A variation where the conductive trace (normal copper) of a PCB has two parallel printed ink resistors alongside. The piezo fabric is held over the three traces in a silicone geometry that compresses when pressed shorting the three traces.

Unique electrical signal sent into points A, B, C, D succesively or sumultaneously. Conductors AB and CD are approx 10% of relaxed surface resistance of Sensor fabric.

Conductor E has near zero resistance andmeasures each of the signals based on increasing pressure to sensor material between elements which reduces resistance causing larger signals of A, B, C, D to be seen on E.

Using ratios of A - B and total Amplitude of A+B position and pressure can be determined.

Measuring ratios of above between signals A-B and C-D location of pressure can be determined between.

If wide contact point or multiple contact points appear along the conductors, a conductive plane behind sensor fabric will allow measurement of signals passed through the fabric to remove ambiguity.

*FIG. 12*

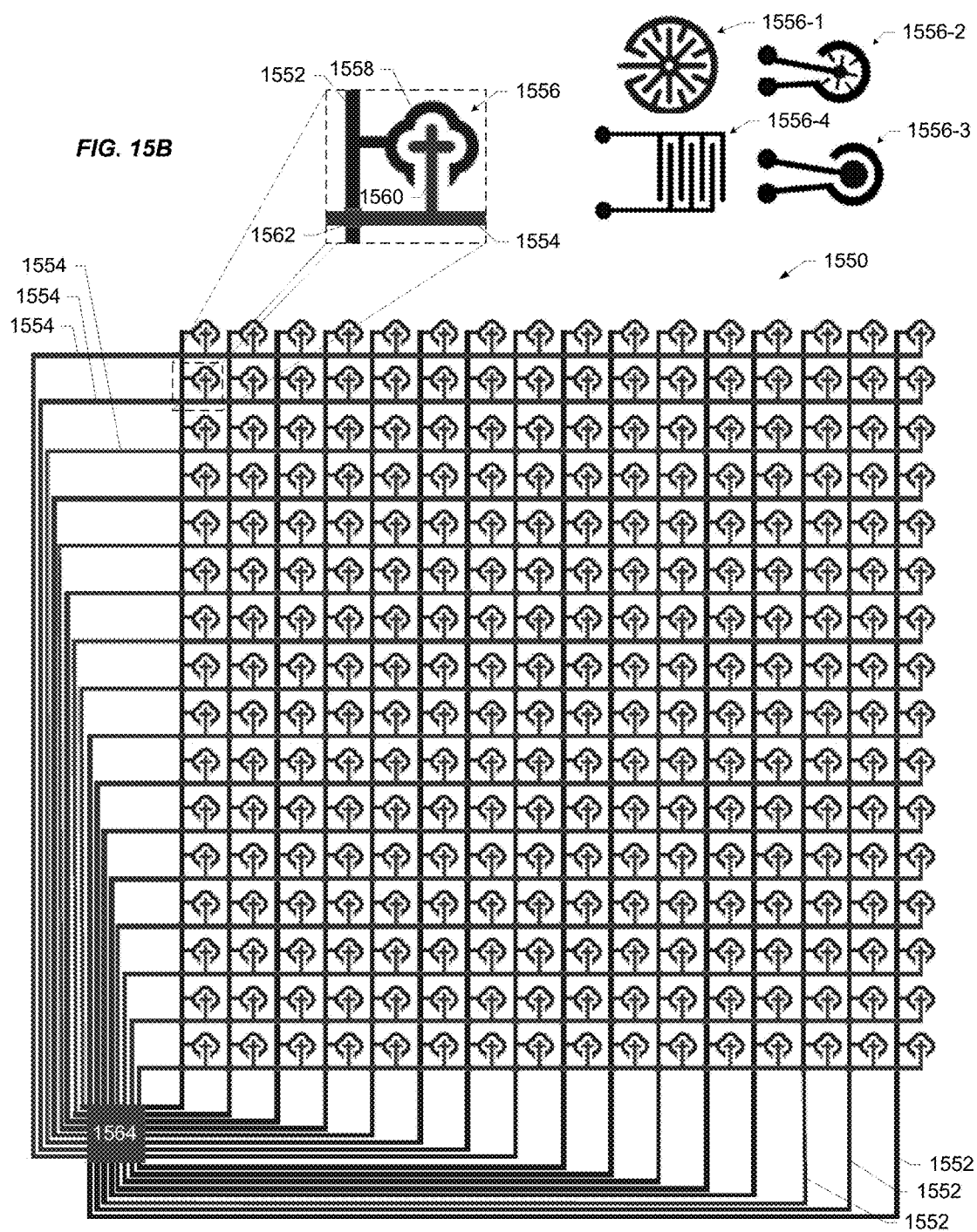

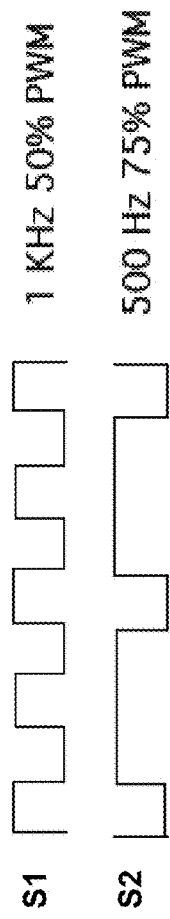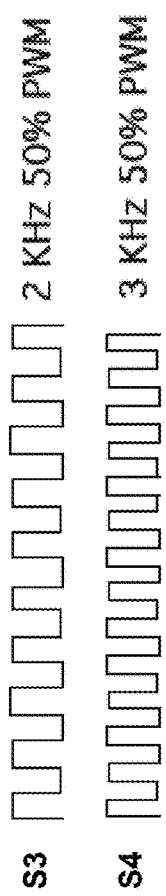
FIG. 17

TWO-DIMENSIONAL SENSOR ARRAYS

RELATED APPLICATION DATA

The present application is a continuation of and claims priority under 35 U.S.C. 120 to U.S. patent application Ser. No. 14/800,538 entitled Two-Dimensional Sensor Arrays filed on Jul. 15, 2015, which is a continuation of U.S. patent application Ser. No. 14/464,551 entitled Two-Dimensional Sensor Arrays filed on Aug. 20, 2014, which is a continuation-in-part application of U.S. patent application Ser. No. 14/299,976 entitled Piezoresistive Sensors and applications filed on Jun. 9, 2014. Both application Ser. No. 14/464,551 and application Ser. No. 14/299,976 are also non-provisionals of and claim priority under 35 U.S.C. 119(e) to U.S. Provisional Patent Application No. 61/993,953 entitled Piezoresistive Sensors and applications filed on May 15, 2014. The entire disclosure of each of the above-mentioned applications is incorporated herein by reference for all purposes.

BACKGROUND

Demand is rapidly rising for technologies that bridge the gap between the computing devices and the physical world. These interfaces typically require some form of sensor technology that translates information from the physical domain to the digital domain. The "Internet of Things" contemplates the use of sensors in a virtually limitless range of applications, for many of which conventional sensor technology is not well suited.

SUMMARY

According to various implementations, sensors and applications of sensors are provided. According to a particular class of implementations, a sensor includes a flexible piezoresistive substrate and two or more conductive traces formed directly on or otherwise integrated with the piezoresistive substrate.

According to some implementations, the sensor includes circuitry configured to receive one or more signals from the conductive traces, and to detect a touch event with reference to the one or more signals. According to some of these implementations, the circuitry is further configured to determine either or both of a location of the touch event, and a magnitude of force of the touch event.

According to some implementations, the piezoresistive substrate is a piezoresistive fabric. According to others, the piezoresistive substrate is a piezoresistive rubber.

According to some implementations, the conductive traces comprise a conductive ink printed on the piezoresistive substrate. According to others, the conductive traces comprise conductive paint deposited on the piezoresistive substrate.

According to some implementations, the conductive traces are formed only on one side of the piezoresistive substrate. According to others, the conductive traces are formed on two opposing sides of the piezoresistive substrate.

According to some implementations, an insulating material formed over a first one of the conductive traces, wherein at least a portion of a second one of the conductive traces is formed over the insulating material and the first conductive trace.

According to some implementations, the two or more conductive traces include a first conductive trace characterized by a first conductivity and a second conductive trace characterized by a second conductivity lower than the first conductivity. The sensor further includes circuitry configured to drive one end of the second conductive trace with a first signal characterized by a first duty cycle, and to drive an opposing end of the second conductive trace with a second signal characterized by a second duty cycle. The circuitry is further configured to receive a mixed signal from the first conductive trace; the mixed signal including contributions from the first and second signals via the piezoresistive substrate. The circuitry is further configured to detect a location of a touch event along a first axis of the second conductive trace with reference to the contributions of the first and second signals to the mixed signal.

According to some implementations, the conductive traces are arranged in a first parallel array of the conductive traces oriented in a first direction formed on one side of the piezoresistive substrate, and second parallel array of the conductive traces oriented at 90 degrees to the first array formed an opposing side of the piezoresistive substrate. The sensor includes circuitry configured to sequentially drive the first array of conductive traces, and to sequentially scan the second array of conductive traces. The circuitry is further configured to determine a location and a magnitude of force for each of one or more touch events with reference to signals received from the second array of conductive traces.

According to some implementations, the conductive traces are arranged in quadrants, and the sensor includes circuitry configured to detect a touch event with reference to signals received from the conductive traces of the quadrants. The circuitry is further configured to determine a location of the touch event, a magnitude of force of the touch event, a speed of motion of the touch event, and a direction of motion of the touch event.

According to some implementations, the conductive traces are arranged in a plurality of conductive trace groups. Each of the conductive trace groups includes two or more of the conductive traces. The resistance between the conductive traces in each of the conductive trace groups varies with force applied to the piezoresistive substrate in a vicinity of the conductive trace group. The sensor includes circuitry configured to receive one or more signals from each of the conductive trace groups and generate control information in response thereto. The control information being for controlling operation of one or more processes or devices in communication with the circuitry.

According to some implementations, the piezoresistive substrate is one or more pieces of piezoresistive fabric integrated with a cap for wearing on a human head. Each of the pieces of piezoresistive fabric has an array of the conductive traces thereon. The sensor includes circuitry configured to detect a touch event with reference to signals received from the conductive traces. The circuitry is further configured to determine a location of the touch event and a magnitude of force of the touch event.

According to a particular class of implementations, a sensor array includes a piezoresistive substrate. A first array of conductive traces is formed on the piezoresistive substrate and aligned with a first dimension of the sensor array. A second array of conductive traces is formed on the piezoresistive substrate and aligned with a second dimension of the sensor array. The sensor array has associated circuitry configured to apply drive signals to the first array of conductive traces, to receive detection signals from the second array of conductive traces, and to determine one or more locations of one or more corresponding touch events on a surface of the sensor array using the drive and detection signals.

According to some implementations, the piezoresistive substrate comprises a flexible piezoresistive material.

According to some implementations, the first and second arrays of conductive traces are formed on only one side of the piezoresistive substrate. According to other implementations, the first and second arrays of conductive traces are formed on both sides of the piezoresistive substrate.

According to some implementations, the conductive traces of the first array are substantially parallel to each other and oriented along the first dimension, and the conductive traces of the second array are substantially parallel to each other and oriented along the second dimension; the first and second dimensions being substantially perpendicular to each other.

According to some implementations, the conductive traces of the first array are characterized by a first conductivity, and the conductive traces of the second array are characterized by a second conductivity higher than the first conductivity. The circuitry is further configured to drive one end of a first conductive trace of the first array with a first signal, and to drive an opposing end of the first conductive trace with a second signal, and to receive a mixed signal from a second conductive trace of the second array. The mixed signal includes contributions from the first and second signals via the piezoresistive substrate, and the circuitry is configured to determine a first location of a first touch event along the first conductive trace with reference to a first value representing the contributions of the first and second signals to the mixed signal.

According to some implementations, the circuitry is further configured to determine one or more additional locations of one or more additional touch events along any of the conductive traces of the first array that are substantially simultaneous with the first touch event with reference to one or more additional values representing one or more additional mixed signals received from one or more of the conductive traces of the second array.

According to some implementations, the circuitry is further configured to determine the first location of the first touch event as being along the first conductive trace and between adjacent conductive traces of the second array. According to some implementations, the circuitry is configured to determine the first location of the first touch event with reference to an additional value representing an additional mixed signal received from an additional conductive trace of the second array.

According to some implementations, the circuitry is further configured to determine a second location of second touch event along the first conductive trace that is substantially simultaneous with the first touch event with reference to the first value and an additional value representing an additional mixed signal received from an additional conductive trace of the second array.

According to some implementations, the circuitry is further configured to drive one end of a third conductive trace of the first array with the first signal, and to drive an opposing end of the third conductive trace with a third signal. The mixed signal also includes additional contributions from the first signal and the third signal corresponding to a second touch event near the third conductive trace that is substantially simultaneous with the first touch event. The circuitry is further configured to generate the first value with reference to the additional contributions from the first and third signals corresponding to the second touch event.

According to some implementations, the circuitry is configured to resolve the first location of the first touch event to one of a plurality of discrete locations associated with the first conductive trace on the surface of the sensor array.

According to some implementations, the circuitry is further configured to determine a force value for each touch event representing a magnitude of a force for the corresponding touch event. According to some implementations, the circuitry is configured to determine the force value for each touch event with reference to an amplitude of a corresponding one of the detection signals.

According to some implementations, each of the conductive traces of the first array coincides with each of the conductive traces of the second array, and the circuitry is further configured to generate a data set for the sensor array with reference to the detection signals. The data set includes a data value for each coincidence of one of the conductive traces of the first array with one of the conductive traces of the second array. The circuitry is configured to determine the one or more locations of the one or more corresponding touch events with reference to the data set.

According to some implementations, the circuitry is further configured to determine a first location of a first touch event near a first coincidence of a first conductive trace of the first array and a second conductive trace of the second array by comparing the data value corresponding to the first coincidence to a threshold. According to some implementations, the threshold is determined with reference to an average of the data values.

According to some implementations, the circuitry is configured to repeat generation of the data set resulting in a plurality of data sets, each data set representing a state of the sensor array for a corresponding period of time. The circuitry is configured to determine the one or more locations of the one or more corresponding touch events with reference to the plurality of data sets. According to some implementations, the circuitry is configured to determine the one or more locations of the one or more corresponding touch events with reference to the plurality of data sets by comparing corresponding data values in successive ones of the data sets.

According to some implementations, the circuitry is configured to generate first and second data values for each coincidence of one of the conductive traces of the first array with one of the conductive traces of the second array. The first data value represents a location of any nearby touch event along the corresponding conductive trace of the first array, and the second data value represents a force associated with the nearby touch event.

According to some implementations, the circuitry is configured to determine a plurality of locations of a plurality of substantially simultaneous touch events on the surface of the sensor array using the drive and detection signals.

According to some implementations, the circuitry is configured to resolve detected touch events to a plurality of discrete locations on the surface of the sensor array.

According to some implementations, the array includes a plurality of force focusing elements each of which is aligned with one of the discrete locations. One or both of the form factor of the force focusing elements and the flexibility of the force focusing elements may be controlled to achieve a corresponding dynamic range of the sensor array. The force focusing elements may be part of the piezoresistive substrate. Alternatively, the array may include an additional substrate adjacent to a combination of the first and second arrays of conductive traces and the piezoresistive substrate. The force focusing elements may be formed on the additional substrate. According to some implementations, the force focusing elements are convex features on the additional substrate. According to some implementations, the additional substrate is part of an environmental protection enclosure for the combination of the first and second arrays of conductive traces and the piezoresistive substrate.

According to some implementations, a first additional substrate is adjacent to a combination of the first and second arrays of conductive traces and the piezoresistive substrate. The first additional substrate has a plurality of structural elements extending therefrom at least partially through the piezoresistive substrate in spaces between the conductive traces. The sensor array further includes a second additional substrate adjacent to the combination of the first and second arrays of conductive traces and the piezoresistive substrate on an opposite side of the combination from the first additional substrate. According to some implementations, the structural elements extend all of the way through the piezoresistive substrate and contact the second additional substrate without force exerted on the surface of the sensor array. According to some implementations, the structural elements extend only part of the way through the piezoresistive substrate. According to some implementations, the first and second additional substrates are part of an environmental protection enclosure for the combination of the first and second arrays of conductive traces and the piezoresistive substrate.

According to some implementations, the piezoresistive substrate includes a plurality of apertures, each of the apertures being aligned with a space between the conductive traces of the first and second arrays. According to some implementations, an additional substrate is adjacent to a combination of the first and second arrays of conductive traces and the piezoresistive substrate. The additional substrate has a plurality of structural elements extending therefrom at least partially through the apertures of the piezoresistive substrate. According to some implementations, the structural elements have a form factor corresponding to a shape of the apertures.

According to some implementations, the conductive traces of the first array are resistive traces, and the circuitry is configured to energize each of the conductive traces of the first array by simultaneously driving opposing ends of the conductive trace with first and second signals, respectively, using a plurality of signal busses. Each signal buss is connected to a plurality of the conductive traces of the first array. The opposing ends of each conductive trace of the first array are connected to a unique pair of the busses. According to some implementations, the conductive traces of the second array are characterized by substantially zero resistance, and at least some of the locations at which the circuitry is configured to determine touch events are along corresponding ones of the conductive traces of the first array and between respective pairs of the conductive traces of the second array.

According to some implementations, the circuitry is configured to resolve detected touch events to a plurality of discrete locations on the surface of the sensor array. The plurality of discrete locations form an array of Y discrete locations along the first dimension by X discrete locations along the second dimension. The first array of conductive traces includes X conductive traces, and the second array of conductive traces includes fewer than Y conductive traces. X and Y are integers greater than zero.

According to some implementations, the circuitry is configured to resolve detected touch events to a plurality of discrete locations on the surface of the sensor array. The plurality of discrete locations form an array of Y discrete locations along the first dimension by X discrete locations along the second dimension. The first array of conductive traces includes X conductive traces. X and Y are integers greater than zero. The sensor array further includes a plurality of busses by which the circuitry applies the drive signals to the first array of conductive traces, the plurality of busses including fewer than X busses.

According to some implementations, each of the conductive traces of the first array coincides with each of the conductive traces of the second array. The sensor array further includes a trace pattern at each coincidence of one of the conductive traces of the first array with one of the conductive traces of the second array. Each trace pattern includes a first trace extending from the corresponding conductive trace of the first array and a second trace extending from the corresponding conductive trace of the second array. The first and second traces have complementary shapes. According to some implementations, one or both of the shapes of the first and second traces and the distance between the first and second traces is controlled to achieve a corresponding dynamic range of the sensor array. According to a particular implementation, the complementary shapes of the first and second traces of each trace pattern are a clover shape and a cruciform shape.

According to another class of implementations, a sensor array includes a first array of conductive traces aligned with a first dimension of the sensor array, and a second array of conductive traces aligned with a second dimension of the sensor array. Piezoresistive material is configured to provide electrical connectivity between the conductive traces of the first and second arrays. The sensor array includes a plurality of force focusing elements each of which is aligned with one of a plurality of discrete locations on a surface of the sensor array. The sensor array has associated circuitry configured to apply drive signals to the first array of conductive traces, to receive detection signals from the second array of conductive traces, and to determine one or more locations of one or more corresponding touch events on the surface of the sensor array using the drive and detection signals. The circuitry is also configured to resolve detected touch events to corresponding ones of the plurality of discrete locations.

According to various implementations, one or both of the form factor of the force focusing elements and the flexibility of the force focusing elements is controlled to achieve a corresponding dynamic range of the sensor array. In some implementations, the force focusing elements are part of the piezoresistive material. In others, the sensor array may include a substrate adjacent to a combination of the first and second arrays of conductive traces and the piezoresistive material; the force focusing elements being formed on the substrate. The force focusing elements may be convex features on the substrate. The substrate may be part of an environmental protection enclosure for the combination of the first and second arrays of conductive traces and the piezoresistive material.

According to some implementations, the sensor array includes a first substrate adjacent to the combination of the first and second arrays of conductive traces and the piezoresistive material on an opposite side of the combination from a second substrate. One of the first substrate or the second substrate has a plurality of structural elements extending therefrom at least partially through the piezoresistive material in spaces between the conductive traces. In some implementations, the structural elements extend all of the way through the piezoresistive material and contact the other of the first substrate or the second substrate without force exerted on the surface of the sensor array. In others, the structural elements extend only part of the way through the piezoresistive material. The first and second substrates may be part of an environmental protection enclosure for the combination of the first and second arrays of conductive traces and the piezoresistive material.

According to some implementations, the piezoresistive material includes a plurality of apertures each of which is aligned with a space between the conductive traces of the first and second arrays. In some implementations, the sensor array includes a first substrate adjacent to the combination of the first and second arrays of conductive traces and the piezoresistive material on an opposite side of the combination from a second substrate. One of the first substrate or the second substrate has a plurality of structural elements extending therefrom at least partially through the apertures of the piezoresistive substrate. The structural elements may have a form factor substantially conforming to a shape of the apertures.

According to some implementations, the piezoresistive material is a flexible piezoresistive material. In some implementations, the first and second arrays of conductive traces may be formed on the piezoresistive material; either on only one side of the piezoresistive material, or on both sides of the piezoresistive material. In others, one or both of the first and second arrays of conductive traces may be formed on one or more substrates adjacent to the piezoresistive material.

According to another class of implementations, a sensor array includes a first array of conductive traces aligned with a first dimension of the sensor array. The conductive traces of the first array are characterized by a first conductivity. The sensor array includes a second array of conductive traces aligned with a second dimension of the sensor array. The conductive traces of the second array are characterized by a second conductivity higher than the first conductivity. A piezoresistive material provides electrical connectivity between the conductive traces of the first and second arrays. Associated circuitry is configured to apply drive signals to the first array of conductive traces, to receive detection signals from the second array of conductive traces, and to determine one or more locations of one or more corresponding touch events on a surface of the sensor array using the drive and detection signals. The circuitry is further configured to drive one end of a first conductive trace of the first array with a first signal, and to drive an opposing end of the first conductive trace with a second signal. The circuitry receives a mixed signal from a second conductive trace of the second array. The mixed signal includes contributions from the first and second signals via the piezoresistive material. The circuitry is further configured to determine a first location of a first touch event along the first conductive trace with reference to a first value representing the contributions of the first and second signals to the mixed signal.

According to some implementations, the circuitry is further configured to determine one or more additional locations of one or more additional touch events along any of the conductive traces of the first array that are substantially simultaneous with the first touch event with reference to one or more additional values representing one or more additional mixed signals received from one or more of the conductive traces of the second array.

According to some implementations, the circuitry is further configured to determine the first location of the first touch event as being along the first conductive trace and between adjacent conductive traces of the second array. According to some implementations, the circuitry is configured to determine the first location of the first touch event with reference to an additional value representing an additional mixed signal received from an additional conductive trace of the second array.

According to some implementations, the circuitry is further configured to determine a second location of second touch event along the first conductive trace that is substantially simultaneous with the first touch event with reference to the first value and an additional value representing an additional mixed signal received from an additional conductive trace of the second array.

According to some implementations, the circuitry is further configured to drive one end of a third conductive trace of the first array with the first signal, and to drive an opposing end of the third conductive trace with a third signal. The mixed signal also includes additional contributions from the first signal and the third signal corresponding to a second touch event near the third conductive trace that is substantially simultaneous with the first touch event. The circuitry is further configured to generate the first value with reference to the additional contributions from the first and third signals corresponding to the second touch event.

According to some implementations, the circuitry is configured to resolve the first location of the first touch event to one of a plurality of discrete locations associated with the first conductive trace on the surface of the sensor array.

According to some implementations, the conductive traces of the first array are resistive traces, and the circuitry is configured to energize each of the conductive traces of the first array by simultaneously driving opposing ends of the conductive trace with first and second signals, respectively, using a plurality of signal busses. Each signal buss is connected to a plurality of the conductive traces of the first array. The opposing ends of each conductive trace of the first array are connected to a unique pair of the busses. According to some implementations, the conductive traces of the second array are characterized by substantially zero resistance, and at least some of the locations at which the circuitry is configured to determine touch events are along corresponding ones of the conductive traces of the first array and between respective pairs of the conductive traces of the second array.

According to some implementations, the circuitry is configured to resolve detected touch events to a plurality of discrete locations on the surface of the sensor array. The plurality of discrete locations form an array of Y discrete locations along the first dimension by X discrete locations along the second dimension. The first array of conductive traces includes X conductive traces, and the second array of conductive traces includes fewer than Y conductive traces. X and Y are integers greater than zero.

According to some implementations, the circuitry is configured to resolve detected touch events to a plurality of discrete locations on the surface of the sensor array. The plurality of discrete locations forms an array of Y discrete locations along the first dimension by X discrete locations along the second dimension. The first array of conductive traces includes X conductive traces. X and Y are integers greater than zero. The sensor array further includes a plurality of busses by which the circuitry applies the drive signals to the first array of conductive traces. The plurality of busses includes fewer than X busses.

According to some implementations, the piezoresistive material is a flexible piezoresistive substrate. According to some implementations, the first and second arrays of conductive traces are formed on the flexible piezoresistive substrate. According to some implementations, the first and second arrays of conductive traces are formed on only one side of the flexible piezoresistive substrate. According to others, the first and second arrays of conductive traces are formed on both sides of the flexible piezoresistive substrate. According to some implementations, one or both of the first and second arrays of conductive traces are formed on one or more additional substrates adjacent to the flexible piezoresistive substrate.

As will be appreciated by those of skill in the art, various combinations of the foregoing features and functionalities are within the scope of this disclosure. A further understanding of the nature and advantages of various implementations may be realized by reference to the remaining portions of the specification and the drawings.

BRIEF DESCRIPTION OF THE DRAWINGS

FIGS. 1A-1D illustrate a particular sensor configuration.
FIG. 7 illustrates another sensor configuration and a technique for acquiring sensor data.
FIG. 8 illustrates various sensor configurations.
FIG. 12 illustrates another sensor configuration and a technique for acquiring sensor data.
FIGS. 15A and 15B are simplified representations of two-dimensional sensor arrays.
FIG. 17 illustrates examples of drive signals for use with the two-dimensional sensor array of FIG. 16.

DETAILED DESCRIPTION

Figure 2A:
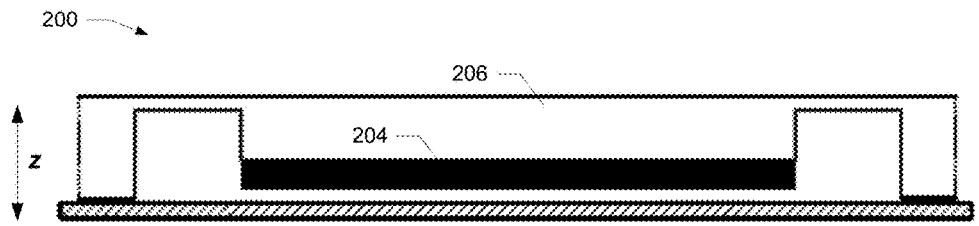
FIGS. 2A-2D illustrate another sensor configuration.

Sensors incorporating piezoresistive materials are described in this disclosure. Specific implementations are described below including the best modes contemplated. Examples of these implementations are illustrated in the accompanying drawings. However, the scope of this disclosure is not limited to the described implementations. Rather, this disclosure is intended to cover alternatives, modifications, and equivalents of these implementations. In the following description, specific details are set forth in order to provide a thorough understanding of the described implementations. Some implementations may be practiced without some or all of these specific details. In addition, well known features may not have been described in detail to promote clarity.

Piezoresistive materials include any of a class of materials that exhibits a change in electrical resistance in response to mechanical force or pressure applied to the material. One class of sensors includes piezoresistive material that is held or otherwise supported (e.g., within a silicone key or control pad) in proximity to conductive traces arranged on a substrate (e.g., a printed circuit board (PCB)). Another class of sensors includes conductive traces formed directly on or otherwise integrated with a flexible substrate of piezoresistive material, e.g., a piezoresistive fabric or other flexible material. When force or pressure is applied to either type of sensor, the resistance between traces connected by the piezoresistive material changes in a time-varying manner that is representative of the applied force. A signal representative of the magnitude of the applied force is generated based on the change in resistance. This signal is captured via the conductive traces (e.g., as a voltage or a current), digitized (e.g., via an analog-to-digital converter), processed (e.g., by an associated processor or controller or suitable control circuitry), and mapped (e.g., by the associated processor, controller, control circuitry, or other device or process) to a control function that may be used in conjunction with virtually any type of process, device, or system. In some implementations, arrays of conductive traces having various configurations are used to determine the location, direction, and/or velocity of the applied force in one or more dimensions (e.g., in addition to the magnitude of the force or pressure).

A particular class of implementations builds on designs described in U.S. patent application Ser. No. 12/904,657 entitled Foot-Operated Controller, now U.S. Pat. No. 8,680,390, and U.S. patent application Ser. No. 13/799,304 entitled Multi-Touch Pad Controller, published as U.S. Patent Publication No. 2013/0239787, the entire disclosures of both of which are incorporated herein by reference for all purposes. In some of these implementations the piezoresistive material is held adjacent (e.g., in contact with or just off) the conductive traces in a flexible key or control pad structure constructed of, for example, silicone. By controlling the geometry of the silicone, the pattern and density of the conductive traces, and the distance of the piezoresistive material from the trace pattern, a variety of sensors can be constructed that have very different response curves and dynamic ranges that are appropriate for a wide range of different applications. It should be noted that the following sensor designs may employ any of the configurations and techniques described in the attached disclosures in various combinations.

FIGS. 1A-1C illustrate a particular sensor configuration 100 useful for implementing the keys of an electronic keyboard. The depicted sensor configuration is intended to be sensitive to a light touch, but also have a dynamic range that is sufficient to provide a significant range of expressiveness for its musician users. Two piezoresistive components 102 and 104 allow the musician to rock key 106 forward and backward to achieve a variety of desired effects, e.g., note bending, vibrato, etc.

A cantilever structure 108 in silicone key 106 (a webbing element that connects the key to a surrounding framing structure and suspends the key within the structure) allows it to collapse evenly and easily, bringing piezoresistive elements 102 and 104 into contact with the corresponding conductive trace patterns 110 and 112 on PCB 114 with very little pressure, e.g., 30-50 grams. The silicone includes stops 115 that resist the vertical travel of the key and define the placement of piezoresistive components 102 and 104. Stops 115 are configured to reduce the effect of higher magnitude forces on the sensor output. The conductive trace patterns by which the change in resistance is measured are configured as a star or asterisk 116 within a spoked circle 118. The density of the trace pattern, the proximity of the piezoresistive components to the conductive traces, and the configuration of the silicone results in a response curve (FIG. 1D) in which only 30-40 grams of pressure results in a significant drop in resistance. The x-axis of the curve represents kilograms of force and the y-axis represents a linearly scaled representation of the sensor's 7-bit analog-to-digital converter output. The curve flattens out after about 8-10 kg, but provides sufficient dynamic range to allow a significant degree of expressiveness.

Figure 2B:
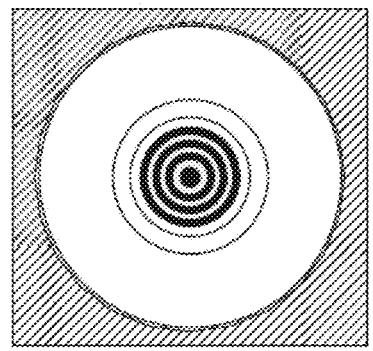
Figure 2C:
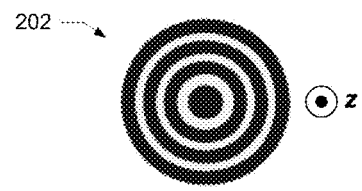
Figure 2D:
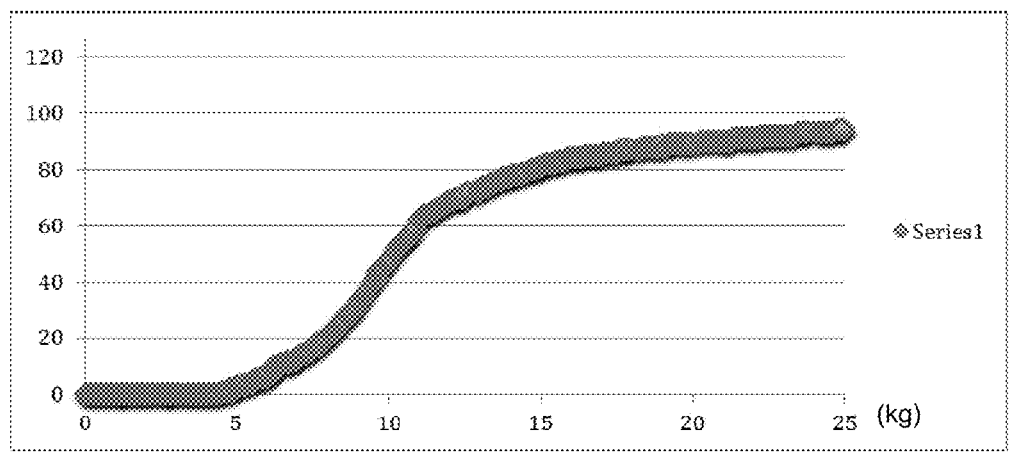

FIGS. 2A-2C illustrate another sensor configuration 200 intended to handle a higher range of force than the sensor configuration of FIGS. 1A-1C. The conductive traces are arranged in a concentric pattern of rings 202 with the change in resistance being measured between adjacent rings. Given its trace pattern density, the spacing of piezoresistive material 204 from the conductive traces, and the overall mechanical resistance of structure 206 to force, this sensor configuration doesn't register much of a response until about 5 kg of force is applied (FIG. 2D). On the other hand, this configuration has useful dynamic range out past 25 kg. Again, the x-axis of the curve represents kilograms of force and the y-axis represents a linearly scaled representation of the sensor's 7-bit analog-to-digital converter output.

Even with careful attention paid to the various elements of the sensor configuration, the dynamic range of a sensor configuration is ultimately limited by the dynamic range of the piezoresistive material itself. According to a particular class of implementations, the range of the piezoresistive material employed is about 40 dB (i.e., about 100:1). This may not be sufficient for some applications. Therefore, according to a particular class of implementations, the sensitivity of a sensor configuration is extended beyond the dynamic range of the piezoresistive material by including multiple piezoresistive components that are spaced at different distances from the conductive traces. According to this approach, the more distant piezoresistive component(s) "take over" when the closer piezoresistive component(s) run out of dynamic range. An example of one such sensor configuration is shown in FIG. 3.

Figure 3:
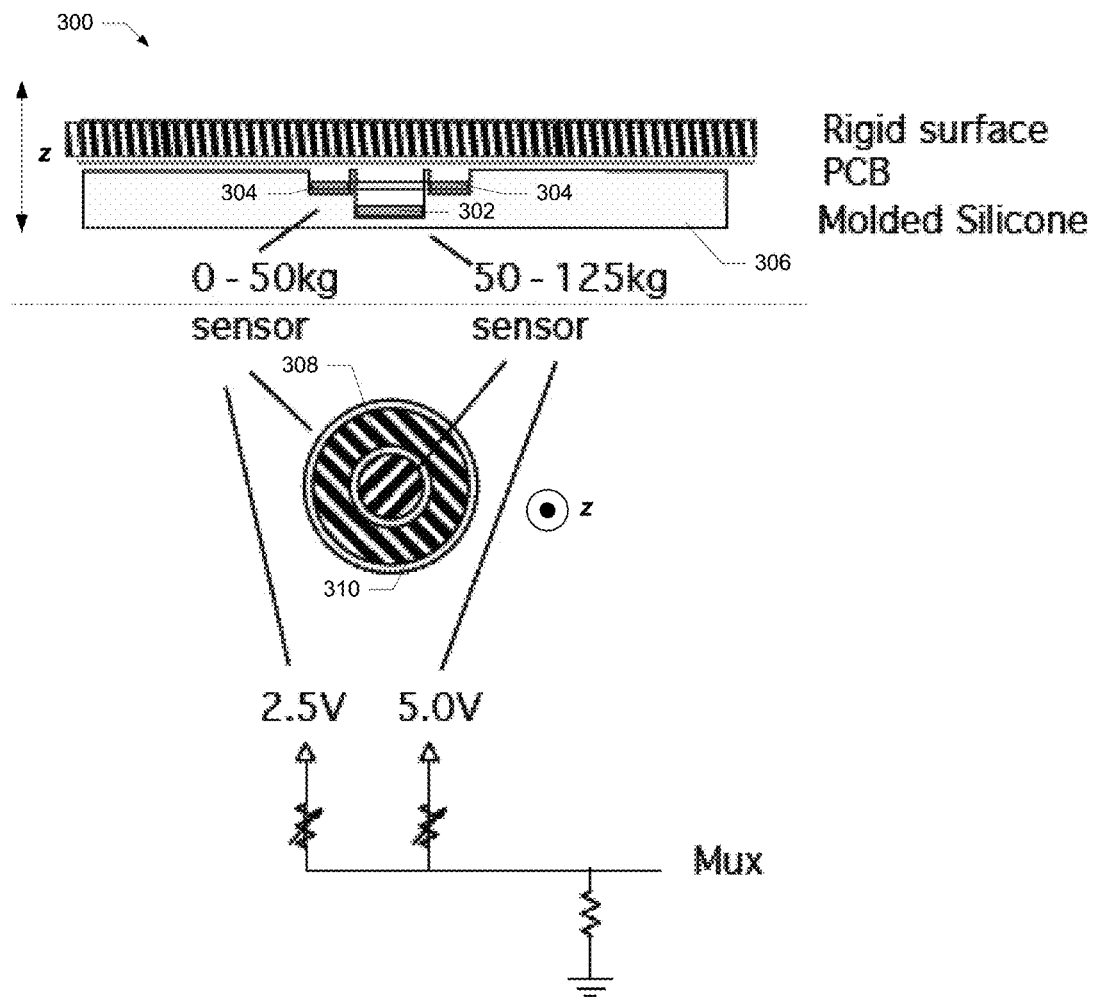
FIG. 3 illustrates yet another sensor configuration.

In sensor 300 of FIG. 3, two distinct piezoresistive components 302 and 304 are supported in a molded silicone structure 306 at different distances from corresponding patterns of conductive traces 308 and 310 on a PCB 312. The piezoresistive components have a concentric configuration (when viewed along the z-axis) in which a circular piezoresistive component is surrounded by an annular piezoresistive component. The conductive traces corresponding to each of the piezoresistive components are arranged as parallel traces in an area similar in shape to the corresponding piezoresistive component. The change in resistance for each set of parallel traces is measured between adjacent traces.

As the silicone in which piezoresistive components 302 and 304 are embedded is compressed, the closer annular component contacts the corresponding conductive traces on the PCB first. As the silicone is further compressed, the more distant circular component then contacts its corresponding conductive traces on the PCB. In the depicted implementation, the silicone and the distances of the piezoresistive components from the PCB are constructed such that the more distant component and the corresponding traces become active around where the closer component and its traces begin to run out of dynamic range. For example, the closer piezoresistive component and the corresponding conductive traces might have a dynamic range covering 0 to about 50 kg of force while the more distant piezoresistive component and its traces might have a dynamic range from about 50 to about 100 kg.

It should be noted that the concentric arrangement of the piezoresistive components and their corresponding trace patterns are merely one example of how multiple components may be configured to achieve a desired dynamic range for a sensor configuration. That is, implementations are contemplated in which the piezoresistive components and their corresponding trace patterns have different shapes and relative arrangements. Implementations are also contemplated in which there are more than two piezoresistive components with corresponding trace patterns. For example, an array might be arranged in a checkerboard pattern in which alternating piezoresistive components and their corresponding trace patterns are configured to cover two or more different parts of the overall dynamic range of the sensor.

Implementations are also contemplated in which the different dynamic ranges associated with the different piezoresistive materials are achieved (at least in part) through variation in the shape, configuration, spacing, and/or conductivity of the different trace patterns. For example, a closely-spaced, dense trace pattern might be used to cover a more sensitive portion of a dynamic range, while a more widely-spaced, sparser trace pattern is used to cover a less sensitive portion of the dynamic range. These types of variations may be done in combination with varying the spacing of the piezoresistive components from the trace patterns and/or the mechanical resistance to applied force of different areas of the sensor.

According to a particular implementation and as shown in FIG. 3, the signals from the multiple piezoresistive components can be read using a shared signal line. In the depicted implementation, the conductive traces corresponding to the closer piezoresistive component covering the lower part of the dynamic range are biased with a lower potential (e.g., 2.5 volts). That is, half of the traces are connected to the lower potential alternating with the other half of the traces being connected to ground via a fixed resistance, as well as providing the output of the sensor (e.g., to an A-to-D converter via a multiplexer). The conductive traces corresponding to the more distant piezoresistive component covering the higher part of the dynamic range are similarly biased with a higher potential (e.g., 5 volts). With this configuration, the dynamic range associated with the closer piezoresistive component (e.g., 304) is represented by the range of 0-2.5 volts, while the dynamic range associated with the more distant piezoresistive component (e.g., 302) is represented by the range of 2.5-5 volts on the same signal line. Reducing the number of signal lines required to acquire this sensor data is advantageous, particularly where there are multiple sensors from which data are acquired.

According to a particular class of implementations, sensors may be implemented using one or more arrays of driven or scanned conductive traces alternating with conductive traces connected to a voltage reference, e.g., ground, through a resistor. Each array is overlaid with a corresponding piezoresistive component. The driven conductive traces in each array are sequentially selected and activated, e.g., by raising its voltage to a known level. When pressure is applied, the driven trace(s) at the point of contact are connected to the adjacent common traces through the piezoresistive material. The voltage at the junction of the common traces and the driven trace(s) is thereby raised. The processor or controller driving the driven traces also sequentially measures the corresponding signal levels to determine whether and where a touch event occurs, and the magnitude of the pressure applied. The processor or controller can also therefore detect the direction and speed of the touch event along the array. As will be appreciated, because of the sequential selection and activation of the traces, such configurations are capable of detecting multiple touch events substantially simultaneously.

Figure 4:
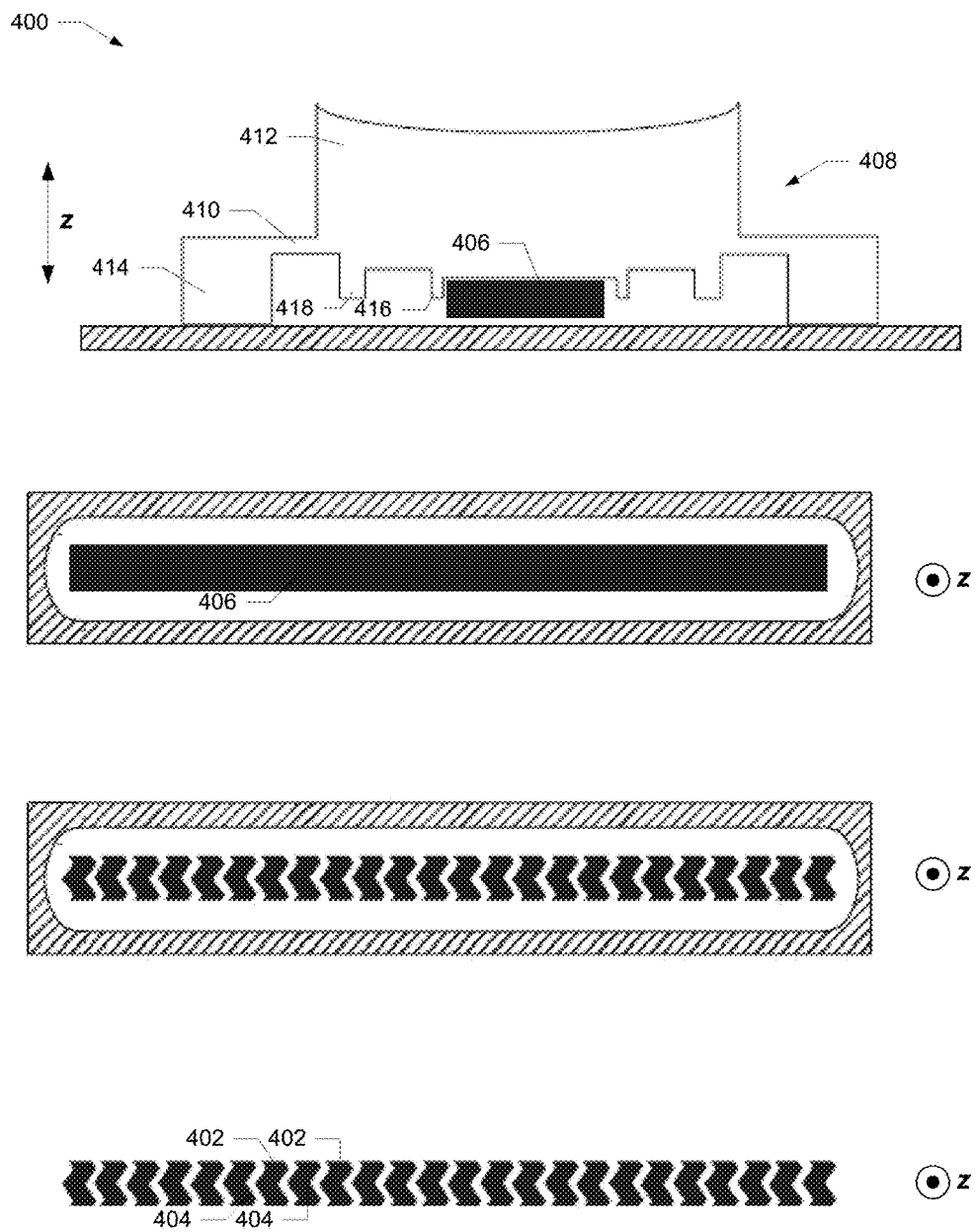
FIG. 4 illustrates still another sensor configuration.
Figure 5:
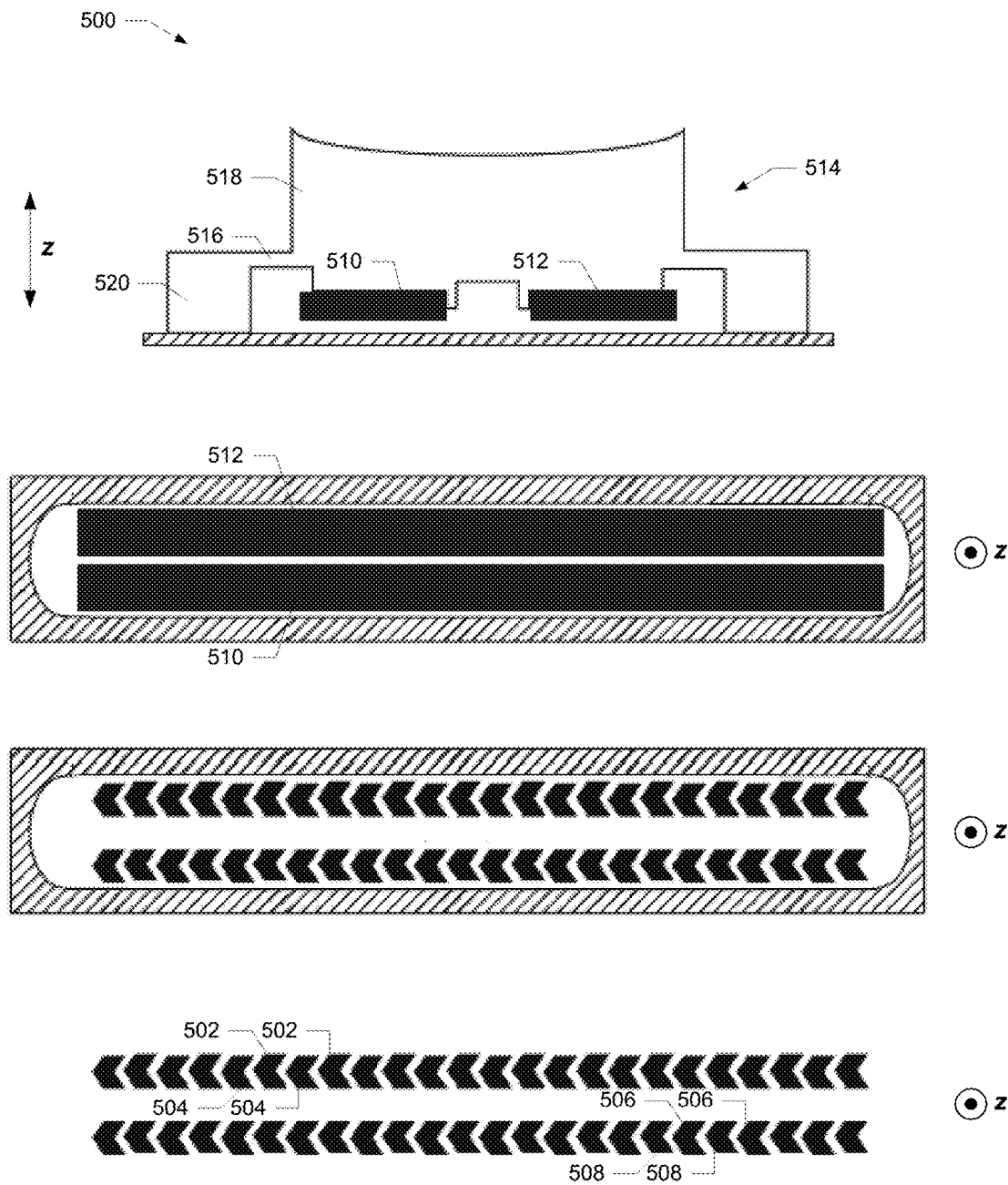
FIG. 5 illustrates a further sensor configuration.

FIG. 4 shows a configuration of such a sensor 400 in which conductive traces 402 and 404 are arranged in a linear array. FIG. 5 shows a configuration 500 in which the conductive traces 502-508 are arranged in two parallel linear arrays. The sensor configurations shown in FIGS. 4 and 5 are designed for use as a fader or slider control with an elongated rectangular key. The linear arrays of conductive traces for each configuration are each aligned with a corresponding piezoresistive component (406 or 510 and 512) supported at a distance from the corresponding traces in a silicone structure (408 or 514). A cantilever structure (410 or 516) in the silicone (i.e., the webbing element that connects and suspends a key part of the structure (412 or 518) to and within a framing part of the structure (414 or 520)) allows it to collapse evenly and easily, bringing the piezoresistive components into contact with the corresponding arrays with very little pressure, e.g., 30-50 grams. The silicone structure may include guides (416) for placement of the piezoresistive components as well as stops (418) that resist the vertical travel of the key. By having two arrays as shown in the configuration of FIG. 5, the associated processor or controller can determine not only the linear location, force, and direction of touch events, but also lateral motion perpendicular to the arrays, e.g., rocking left and right on the key.

According to another class of implementations, conductive traces are printed, screened, deposited, or otherwise formed directly onto or integrated with flexible piezoresistive material. As will be appreciated, this allows for the creation of a sensor or sensor array that fits any arbitrary shape or volume. The piezoresistive material may be any of a variety of woven and non-woven fabrics having piezoresistive properties. And although reference may be made to piezoresistive fabrics, implementations are also contemplated in which the piezoresistive material may be any of a variety of flexible materials (e.g., rubber, or a stretchable fabric such as spandex or open mesh fabrics) having piezoresistive properties. The conductive traces may be formed using any of a variety of conductive inks or paints. Implementations are also contemplated in which the conductive traces are formed using any flexible conductive material that may be formed on the flexible piezoresistive material. It should therefore be understood that, while specific implementations are described with reference to specific materials and techniques, the scope of this disclosure is not so limited.

Both one-sided and two-sided implementations are contemplated, e.g., conductive traces can be printed on one or both sides of the piezoresistive material. As will be understood, two-sided implementations may require some mechanism for connecting conductive traces on one side of the piezoresistive material to those on the other side. Some implementations use vias in which conductive ink or paint is flowed through the via to establish the connection. Alternatively, metal vias or rivets may make connections through the piezoresistive material.

Both single and double-sided implementations may use insulating materials formed on the piezoresistive material and/or the conductive traces. This allows for the stacking or layering of conductive traces and signal lines, e.g., to allow the routing of signal line to isolated structures in a manner analogous to the different layers of a PCB.

Routing of signals on and off the piezoresistive material may be achieved in a variety of ways. A particular class of implementations uses elastomeric connectors (e.g., ZEBRA® connectors) which alternate conductive and non-conductive rubber at a density typically an order of magnitude greater than the width of the conductive traces to which they connect (e.g., at the edge of the material). Alternatively, a circuit board made of a flexible material (e.g., Kapton), or a bundle of conductors may be riveted to the material. The use of rivets may also provide mechanical reinforcement to the connection.

Matching conductive traces or pads on both the piezoresistive material and the flexible circuit board can be made to face each. A layer of conductive adhesive (e.g., a conductive epoxy such as Masterbond EP79 from Masterbond, Inc. of Hackensack, N.J.) can be applied to one of the surfaces and then mated to the other surface. The conductive traces or pads can also be held together with additional mechanical elements such as a plastic sonic weld or rivets. If conductive rivets are used to make the electrical connections to the conductive traces of the piezoresistive material, the conductive adhesive may not be required. Conductive threads may also be used to connect the conductive traces of the piezoresistive material to an external assembly.

According to a particular class of implementations, the piezoresistive material is a pressure sensitive fabric manufactured by Eeonyx, Inc., of Pinole, Calif. The fabric includes conductive particles that are polymerized to keep them suspended in the fabric. The base material is a polyester felt selected for uniformity in density and thickness as this promotes greater uniformity in conductivity of the finished piezoresistive fabric. That is, the mechanical uniformity of the base material results in a more even distribution of conductive particles when a slurry containing the conductive particles is introduced. The fabric may be woven. Alternatively, the fabric may be non-woven such as, for example, a calendared fabric e.g., fibers, bonded together by chemical, mechanical, heat or solvent treatment. Calendared material may present a smoother outer surface which promotes more accurate screening of conductive inks than a non-calendared material.

The conductive particles in the fabric may be any of a wide variety of materials including, for example, silver, copper, gold, aluminum, carbon, etc. Some implementations may employ carbon graphenes that are formed to grip the fabric. Suitable piezoresistive materials may be fabricated using techniques described in U.S. Pat. No. 7,468,332 for Electroconductive Woven and Non-Woven Fabric issued on Dec. 23, 2008, the entire disclosure of which is incorporated herein by reference for all purposes. However, it should again be noted that any flexible material that exhibits a change in resistance or conductivity when pressure is applied to the material and/or on which conductive traces may be printed, screened, deposited, or otherwise formed will be suitable for implementation of sensors as described herein.

Conductive particles may be introduced to the fabric using a solution or slurry, the moisture from which is then removed. According to some implementations, the way in which the moisture is removed from the fabric may also promote uniformity. For example, using an evenly distributed array of vacuum heads or ports to pull the moisture from the fabric reduces the concentrations of conductive particles around individual vacuum heads or ports. The vacuum heads or ports may be arranged in 1 or 2 dimensional arrays; the latter being analogized to a reverse air hockey table, i.e., an array of vacuum ports which pull air in rather than push air out.

Implementations are also contemplated in which the uniformity of the piezoresistive fabric is not necessarily very good. Such implementations may use multiple, closely-spaced sensors operating in parallel, the outputs of which can be averaged to get more accurate and/or consistent readings.

According to a particular class of implementations, conductive traces having varying levels of conductivity are formed on the piezoresistive material using conductive silicone-based inks manufactured by, for example, E.I. du Pont de Nemours and Company (DuPont) of Wilmington, Del., and/or Creative Materials of Ayer, Mass. An example of a conductive ink suitable for implementing highly conductive traces for use with various implementations is product number 125-19 from Creative Materials, a flexible, high temperature, electrically conductive ink. Examples of conductive inks for implementing lower conductivity traces for use with various implementations are product numbers 7102 and 7105 from DuPont, both carbon conductive compositions. Examples of dielectric materials suitable for implementing insulators for use with various implementations are product numbers 5018 and 5036 from DuPont, a UV curable dielectric and an encapsulant, respectively. These inks are flexible and durable and can handle creasing, washing, etc. The degree of conductivity for different traces and applications is controlled by the amount or concentration of conductive particles (e.g., silver, copper, aluminum, carbon, etc.) suspended in the silicone. These inks can be screen printed or printed from an inkjet printer. Another class of implementations uses conductive paints (e.g., carbon particles mixed with paint) such as those that are commonly used for EMI shielding and ESD protection.

Figure 6:
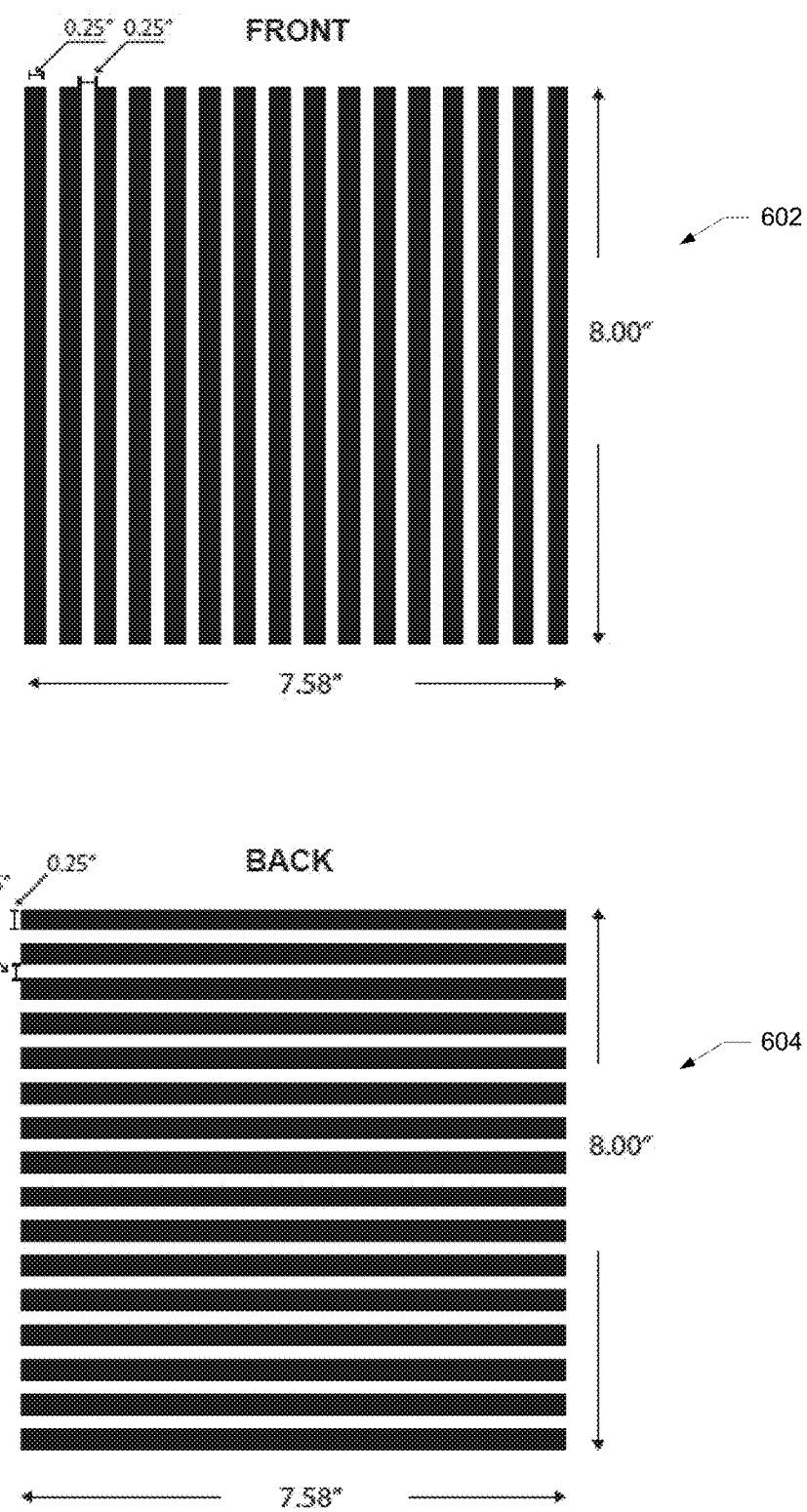
FIG. 6 illustrates a two-sided sensor array.

One example of a two-sided implementation is shown in FIG. 6 and has an array 602 of parallel conductive traces oriented in one direction printed on one side of the piezoresistive fabric, and another array 604 oriented at 90 degrees to the first array printed on the other side of the fabric. This implementation takes advantage of the fact that the piezoresistive fabric is conductive through its thickness (in addition to laterally and across its surface) to implement a pressure sensitive X-Y matrix. By sequentially driving the array on one side of the piezoresistive material and sequentially scanning the array on the other side, both the position and force of a touch event on the array can be detected. Again, because of the sequential selection and activation of the traces, such a configuration is capable of detecting multiple touch events substantially simultaneously. As will be understood, the applications for such a sensor array are virtually limitless.

As will be understood by those of skill in the art, a variety of techniques may be employed to acquire data from sensors constructed as described herein. Some of these techniques may involve a simple measurement of a change in resistance (as determined from a voltage or current) between two conductive traces having the same or similar conductivity. However, for sensors having arrays that include many conductive traces, this may require an unacceptable number of signal lines to route signals both to and from the sensor array. Therefore, according to a particular class of implementations, conductive traces formed on piezoresistive material and having different levels of conductivity are driven and interrogated with signal patterns that reduce the number of signal lines required to achieve sensor configurations that are sensitive to location, pressure, direction, and velocity of applied force.

FIG. 7 illustrates an example of such an implementation intended to provide functionality similar to the sensor of FIG. 5 but with fewer signal lines. Adjacent (in this case substantially parallel) conductive traces are formed on piezoresistive fabric 700 with one (E) being highly conductive, e.g., near-zero resistance, and the other (AB) being less conductive, e.g., about 100 ohms from A to B if the resistance between traces AB and E without pressure is about 1K ohms. The less conductive trace is driven at opposing ends by different signals A and B (e.g., by one or more signal generators). Pressure on the piezoresistive material reduces the resistance between the two traces which, depending on the location, results in different contributions from signals A and B measured in a mixed signal on the highly conductive trace E. The overall amplitude of the mixed signal also increases with pressure.

According to a particular class of implementations, signals A and B are different pulse trains of the same amplitude; e.g., one at 1 kHz, one with a 50% duty cycle, and the other at 500 Hz with a 75% duty cycle as shown in FIG. 7. The phases of the two pulse trains are synchronized to avoid zero volts being applied to the less conductive trace. Location information can be derived from the mixed signal measured on E as follows. The signal on E is sampled by an A/D converter (e.g., oversampled by a factor of two or more relative to the frequency of the inputs). An inexpensive, general-purpose processor may be employed that can read up to 40 signals with up to 10-bits of resolution, and take 500K samples per second. The same general processor may drive the conductive traces. Thus, arrays with large numbers of sensors may be constructed relatively inexpensively.

The processor evaluates specific amplitudes at specific times that are correlated with the values of signals A and B at those times. The relative contribution from each signal is determined by selecting closely-spaced samples of the mixed signal at times when the respective signals are each known to have a particular value or characteristic, e.g., full amplitude. The ratio of those two measurements represents the relative contributions of each signal to the mixed signal that, in turn, can be mapped to a location between the end points of the AB trace. The pressure or force of the touch event can be determined by measuring peak values of the sampled mixed signal. With this configuration, a pressure sensitive slider can be implemented with only 3 signal lines required to drive the traces and acquire the signal (as opposed to the many signal lines associated with the linear array of traces in sensor configuration of FIG. 5.

According to a particular implementation shown in FIG. 7, a second conductive trace CD runs parallel to trace E on the opposing side from trace AB. As with trace AB, the opposing ends of this additional conductive trace are driven with signals C and D; each different from the other as well as signals A and B. As a result, the mixed signal on trace E includes contributions from each of the four signals. This mixed signal may be processed for one or both of the signal pairs in a manner similar to that described above to determine the location of a touch event along the longitudinal axis of the array. The relative amplitudes of the two signal pairs (e.g., derived by measuring amplitudes for the combination of signals A and B and the combination of signals C and D) represent the location of the touch event along the latitudinal axis of the array. This enables measuring of the location of the touch event in two dimensions. This might enable, for example, the capture of a sideways rocking motion of a finger on a key. As with the example described above, the pressure of the touch event may be determined by measuring peak values of the sampled mixed signal. In this way, an XYZ sensor may be implemented with five traces (with the Z axis being represented by the force of the touch event).

FIG. 8 shows a variety of trace patterns formed on flexible piezoresistive material, e.g., conductive ink on piezoresistive fabric, for different applications. Trace pattern 802 implements a four-quadrant sensor that operates similarly to those described, for example, in U.S. Pat. No. 8,680,390 and U.S. Patent Publication No. 2013/0239787, incorporated herein by reference above. In addition to detecting the occurrence and force of touch events, such a sensor may also be configured to determine the direction and velocity of motion over the quadrants including, for example, both linear and rotational motion relative to the surface of the sensor. Trace patterns 803 (clover and cruciform configuration), 804, 806 and 808 implement sensors that measure the occurrence and force of touch events with different response curves and dynamic ranges resulting from the different configurations.

Trace pattern 810 is used to illustrate both single and double-sided implementations that use either vias or rivets through the piezoresistive material (e.g., configuration 812), insulating materials formed over conductive traces (e.g., configuration 814), or both. As discussed above, such mechanisms enable complex patterns of traces and routing of signals in a manner analogous to the different layers of a PCB.

Figure 9:
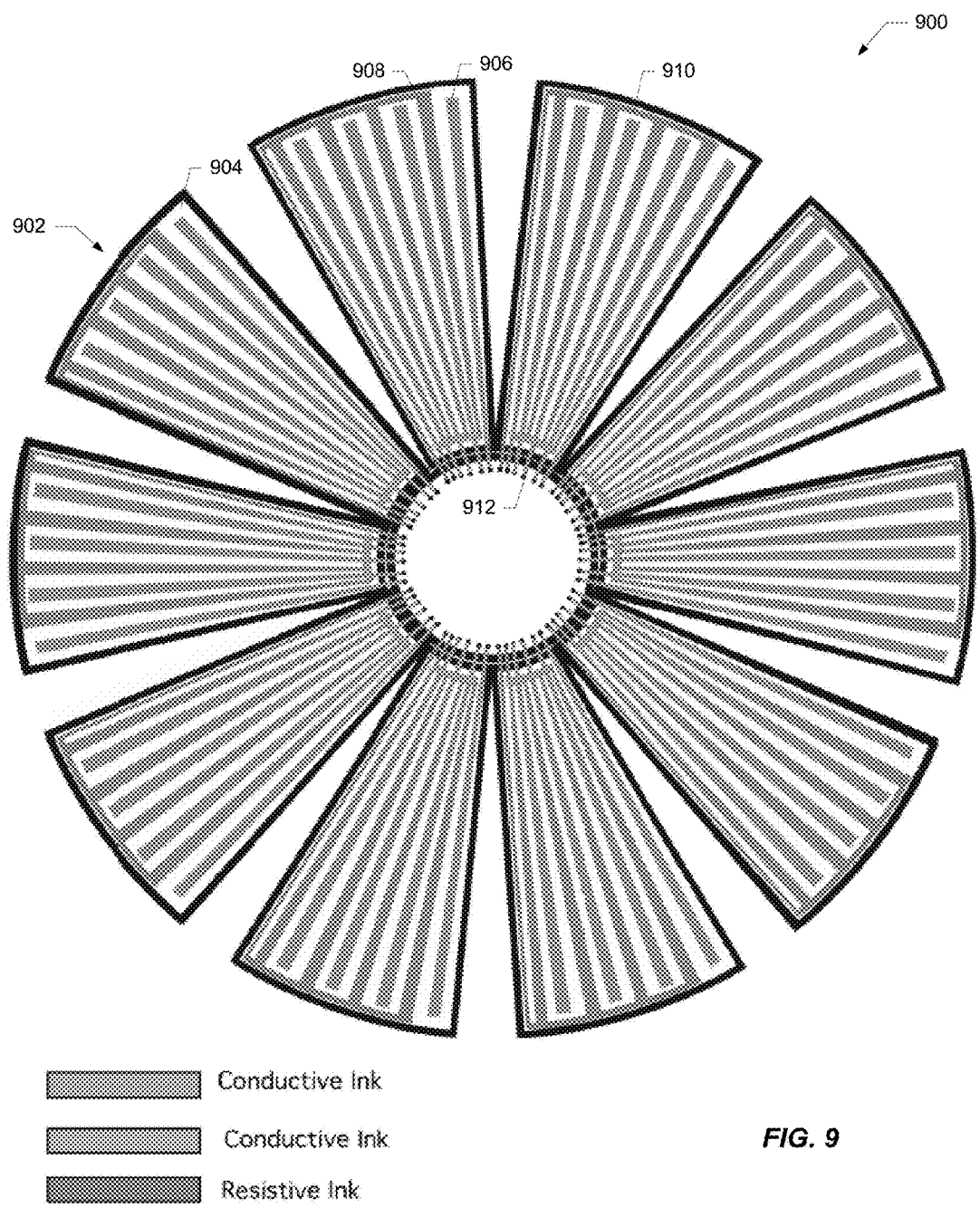
FIG. 9 illustrates a hemispherical sensor array.

FIG. 9 illustrates a sensor array 900 for inclusion in a helmet or skull cap worn on a human head, e.g., for measuring the force and location of impacts. Such an array might be suitable, for example, for capturing data regarding contact events on sports helmets or other protective gear designed to protect the human head. This information might be useful during the design and testing phases of such protective gear, as well as gathering data once in use. It should be noted that sensors located in a cap that covers areas of the skull provide information about contact events that actually reach the skull. This is to be contrasted with some existing systems that instead measure the contact event to the protective helmet. Each flap 902 is constructed from a flexible piezoresistive material 904 with a pattern of conductive traces formed on the material, e.g., conductive ink printed on piezoresistive fabric. As with the traces of FIG. 7, some of the traces 906 are highly conductive and alternate with traces 908 having lower conductivity.

Like trace AB of FIG. 7, traces 908 on each flap are driven at opposing ends with signals having the same amplitude and different duty cycles. The same pair of signals may be used for all of the flaps. These signals are routed to the opposing ends of traces 908 from the center of the array via traces 910 and 912. As can be seen, trace 912 on each flap crosses over traces 906 from which trace 912 is insulated, e.g., from insulators (not shown) printed or formed over the underlying conductive traces.

Each of the signals on traces 906 is routed to the center of the array and represents the mixing of the signals on adjacent traces 908. The location and magnitude of touch events along longitudinal axes of the traces (e.g., the radial coordinate from the center of the array) may be determined from the mixed signal as described above with reference to FIG. 7. The angular coordinate may be determined from the conductive trace 906 that registers the touch event.

Figure 10:
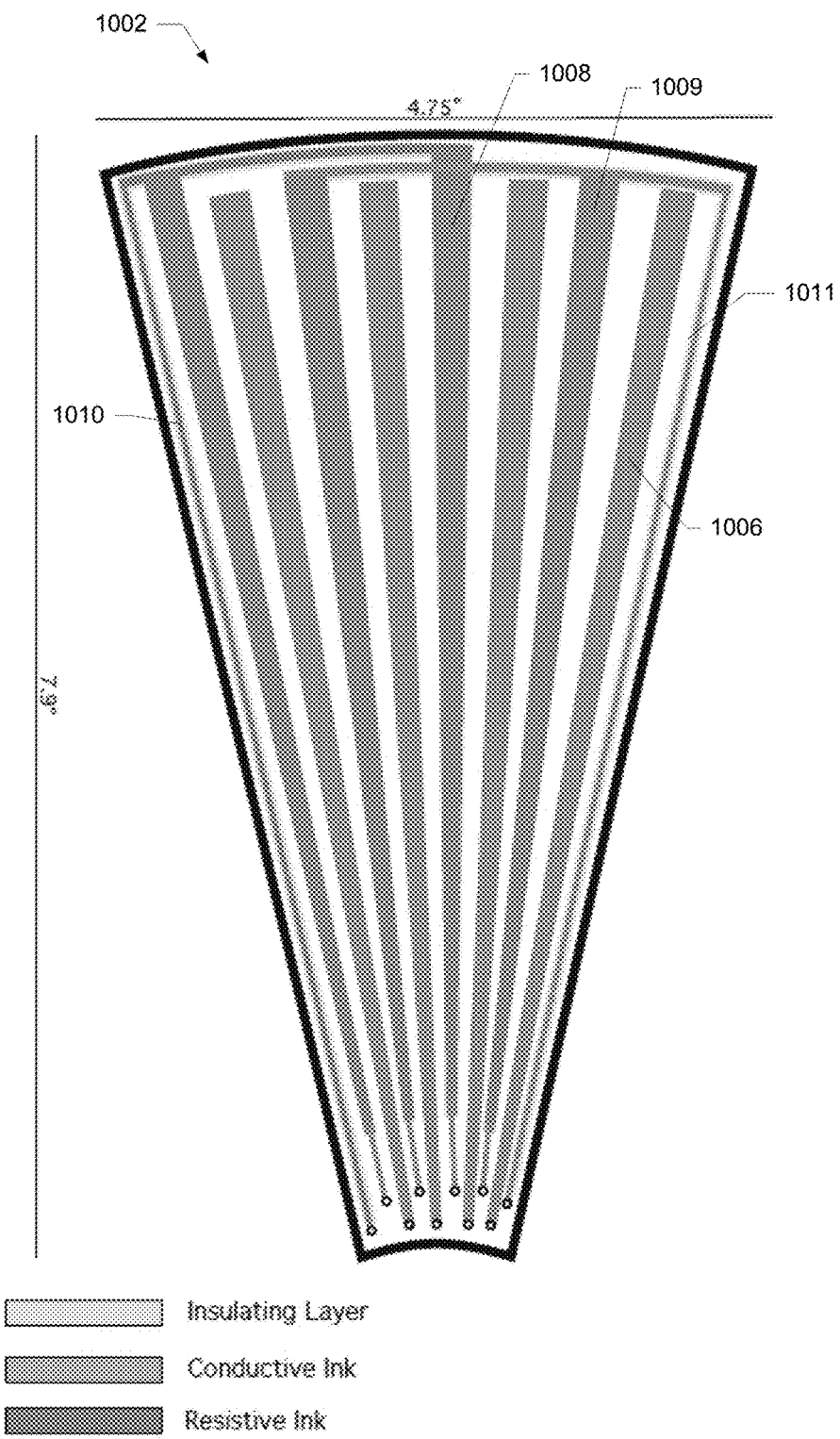
FIG. 10 illustrates a portion of a hemispherical sensor array.

An alternative implementation of the flap for such a sensor array similar to the one depicted in FIG. 9 is shown in FIG. 10. Flap 1002 includes an alternating pattern of highly conductive traces 1006 and traces 1008 and 1009, both of which are characterized by a lower conductivity than traces 1006. However, instead of driving each of the lower conductivity traces with the same signal pair as described above with reference to FIG. 9, traces 1008 are driven with one signal pair (using trace 1010) and traces 1009 are driven with another (using traces 1011). This is analogous to the addition of the second conductive trace CD described above with reference to FIG. 7. That is, the mixed signals present on each of traces 1006 can be processed as described above with reference to the configuration of FIG. 7 to determine the relative contributions from the 4 signals driving adjacent traces 1008 and 1009, and therefore the location of an applied force in two dimensions, e.g., along the longitudinal axes of the traces (the radial coordinate from the center of the array), and the latitudinal axes of the traces (the angular coordinate relative to the center of the array). The magnitude of the applied force may also be determined as described above with reference to FIG. 7.

Figure 11:
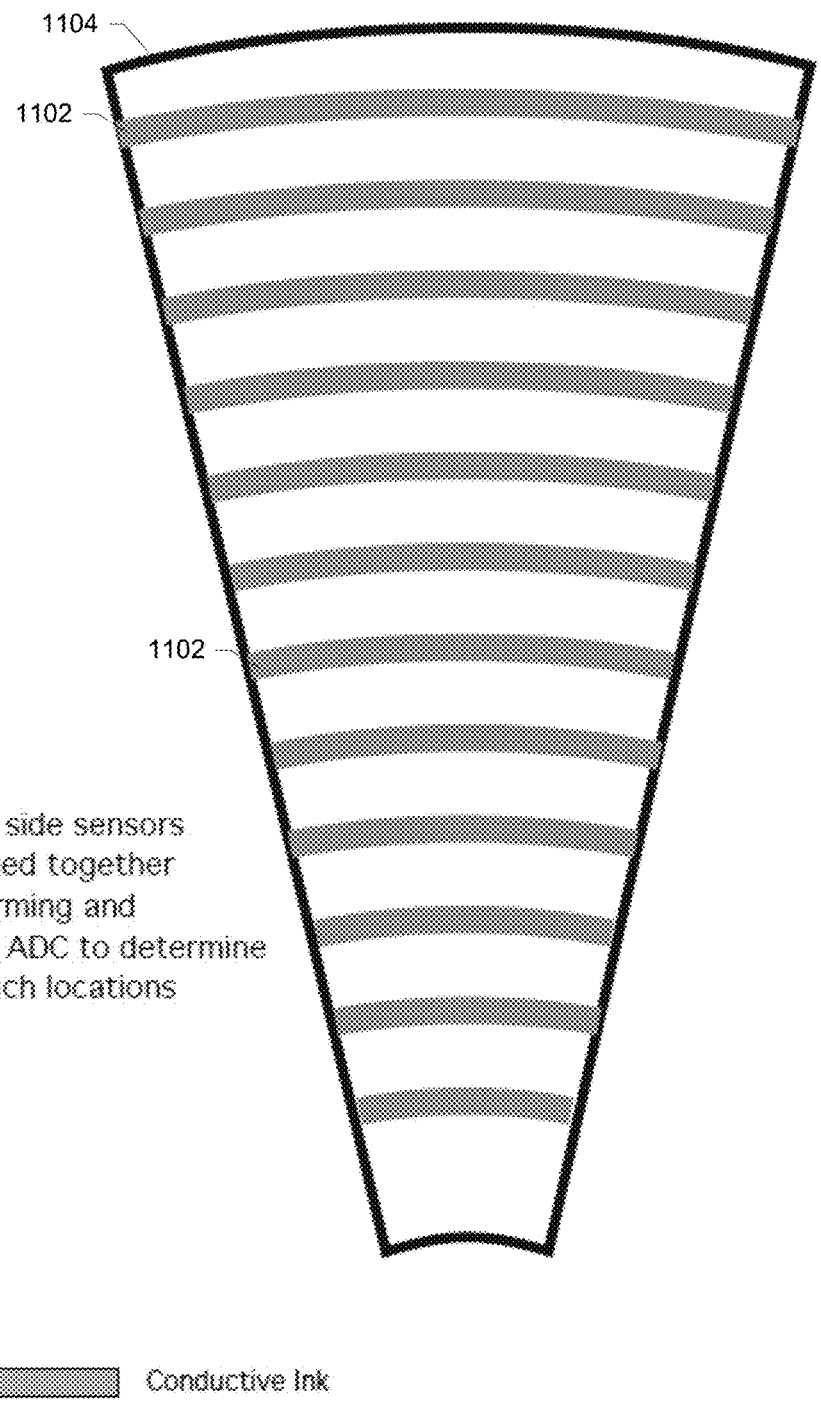
FIG. 11 illustrates a portion of a hemispherical sensor array.

FIG. 11 illustrates a pattern of conductive traces 1102 on a flap 1104 that may be on the other side of the flap from the trace patterns of FIG. 9 or 10. Traces 1102 may be used in conjunction with the techniques described above to disambiguate between multiple simultaneous touch events. For example, as discussed above, the mixed signals on traces 1006 of FIG. 10 include contributions from adjacent traces 1108 and 1109 as affected by the location and magnitude of an applied force or touch event. However, if there were two simultaneous touch events on the same flap, there would be ambiguity as to the locations of the events as the mixing of the resulting signals would, in effect, perform a kind of averaging that would result in a reading that doesn't accurately represent the location of either event. Traces 1102 on the other side of the flaps may be configured to address this issue.

According to a particular implementation in which multiple flaps 1104 are configured as shown in FIG. 9, a roughly hemispherical shape may be formed by bringing the long edges of the flaps together. Traces 1102 can be connected to corresponding traces on adjacent flaps to form something analogous to latitude lines around the hemisphere. Signals on each of these traces can be read (e.g., by an analog-to-digital converter (ADC) and an associated processor) to identify the places of activity on the opposite side of the fabric. For example if two pressure points are along the same longitudinal trace on the other side of the fabric (e.g., traces 1006) they may not be distinguishable. However, by examining the latitudinal traces it can be determined where the points of contact are based upon increased signal level present. Locations between the latitudinal traces can be determined using relative signal strength.

As will be appreciated, the sampling rate of the latitudinal conductors may be sufficiently fast to detect multiple touch events at different latitudes substantially simultaneously. As will also be appreciated, if the traces 1102 on all of the flaps are connected as described, the information derived from these traces will only give a latitude for each of the multiple touch events. However, this can be combined with information derived from traces on the other side of the flaps (e.g., as discussed above with reference to FIGS. 9 and 10) to determine the longitudinal (e.g., east to west) coordinates of the events. In an alternative implementation, traces 1102 on each flap may be processed independently of the other flaps with the introduction of additional signal lines.

As mentioned above, the description of specific implementations herein is intended to provide illustrative examples rather than limit the scope of this disclosure. And although two classes of sensors have been described herein, it should be understood that at least some of the techniques and configurations described may be employed by either class of sensor. For example, the technique for driving and reading conductive traces described above with reference to FIG. 7 is not limited to implementations in which the conductive traces are formed on the piezoresistive material. That is, the same principle may be applied to the class of sensors in which piezoresistive material is supported (e.g., within a silicone key or control pad) adjacent conductive traces that are arranged on a substrate (e.g., a printed circuit board (PCB)) rather than formed directly on or otherwise integrated with the piezoresistive material. An example of such an implementation is illustrated in FIG. 12.

In the depicted implementation, trace E (which may be, for example, copper) is formed on PCB 1202 with two adjacent and parallel traces AB and CD (which may be, for example, printed ink resistors). The resistance of trace E is near zero. For some applications, the resistance of traces AB and CD may be about 10% of the relaxed surface resistance of piezoresistive material 1204 over the distance between those traces and trace E. Piezoresistive material 1204 is held adjacent the three traces in a compressible structure 1206 (which may be, for example, silicone). Piezoresistive material 1204 may be held at a distance from the traces or in contact with them.

As described above with reference to FIG. 7, four unique signals A, B, C and D drive the corresponding ends of traces AB and CD. The resulting mixed signal on trace E may then be processed to determine the location, direction, velocity and force of a touch event on the surface of structure 1206.

For implementations that employ arrays of sensors and/or in which the magnitude of applied forces captured by sensors is important, the uniformity of the piezoresistive material can be critical. Therefore, a class of test systems is provided that is configured to measure changes in resistance of a piezoresistive material at a number of closely spaced locations. According to a particular subclass of test systems, an array of conductive traces is provided on a substantially rigid substrate such as, for example, a printed circuit board (PCB). A sheet of piezoresistive material (e.g., a piezoresistive fabric as described herein) to be tested is placed over the PCB in contact with the conductive traces, and pairs of the conductive traces are sequentially activated such that the signals representative of the resistance of the piezoresistive material are captured at an array of locations (e.g., by associated circuitry on the PCB). By introducing known forces on the piezoresistive material, the response of the piezoresistive material may be characterized over its surface and/or volume, thus yielding test data representing how uniformly the material behaves in response to applied force.

As will be appreciated, such information would be extremely useful for manufacturers of piezoresistive materials in designing and evaluating new materials as well as classifying products with regard to their uniformity characteristics. Such information would also be useful to designers of systems incorporating such materials (e.g., sensor systems) in that they will be able to select materials that have a level of uniformity that is appropriate for their particular application.

Figure 13:
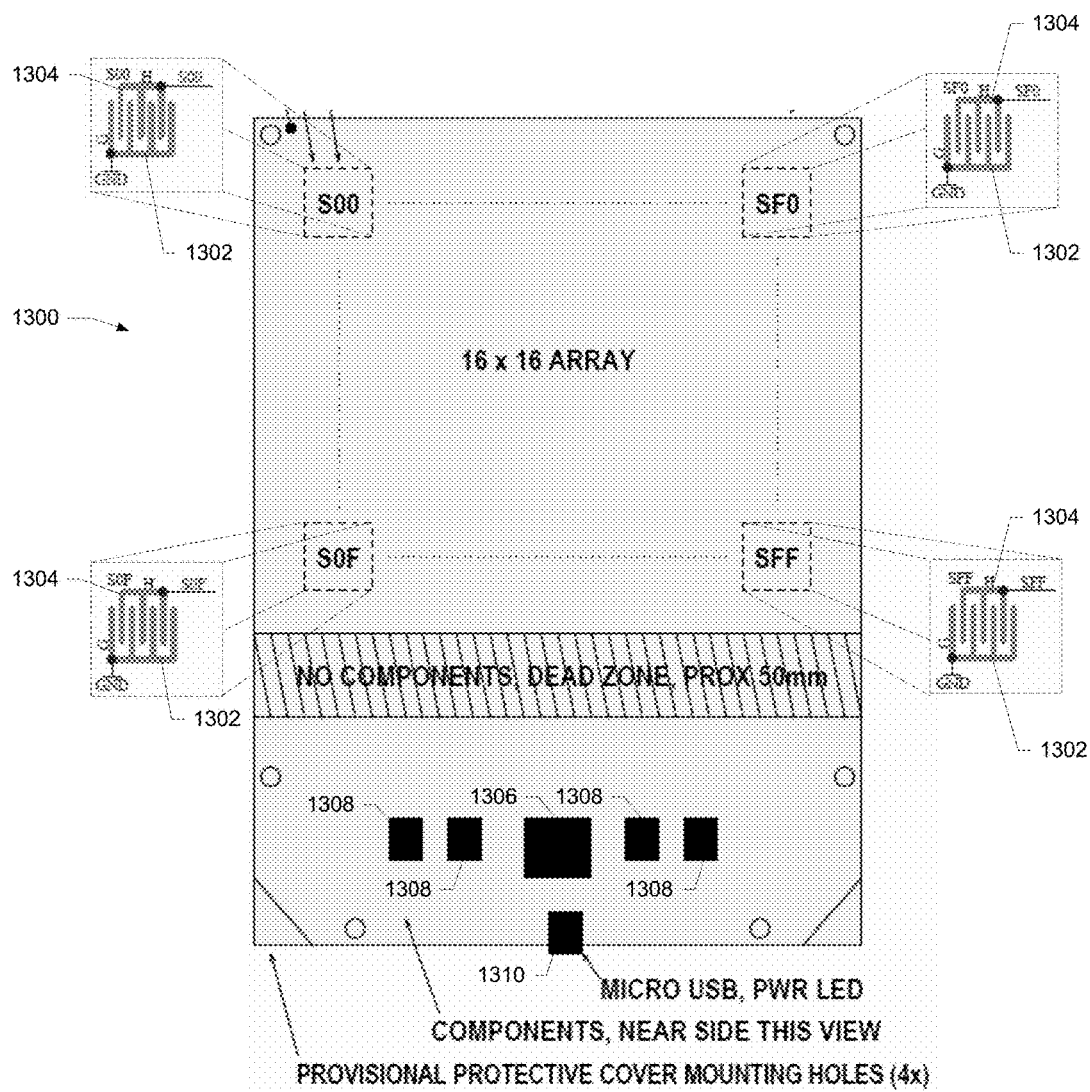
FIG. 13 illustrates a test system for piezoresistive materials.

An example of such a test system 1300 is shown in FIG. 13. Pairs of interlaced conductive traces 1302 and 1304 are formed on a PCB to provide an array of 256 locations at which the resistance of a sheet of piezoresistive material placed in contact with the array (not shown) may be measured. As will be appreciated the number of locations, the arrangement of the array, and the configuration of the conductive traces may vary significantly (e.g., see examples described above) for different implementations depending on a number of factors such as, for example, the dynamic range required, the shape, size, and/or construction of the piezoresistive material to be tested, etc. The Simplified Block Diagram included in FIG. 13 illustrates the connection and control of each pair of traces. Trace 1302 is connected to ground (GND). Trace 1304 is pulled up to a bias voltage (VBIAS) of 3.3 volts via a variable impedance and is also the trace by which the resistance measurement of the material under test at that location of the array is made.

Control circuitry 1306 (which may include, for example, a central processing unit (CPU) and associated circuitry) sequentially reads the signals at each of traces 1304 in the array by controlling multiplexers 1308. The measurements are digitized and serialized and transmitted to a computing device, e.g., a desktop or laptop computer, a tablet, a smart phone, etc. (not shown), via USB port 1310. As will be appreciated, similar conversion and processing circuitry may be used with any of the sensor configurations described herein. As force is exerted on a piezoresistive material under test in contact with a particular pair of traces, the resistance of the material (represented by variable resistor 1312) changes, and the resulting signal is captured by control circuitry 1306. According to some implementations, additional structures may be formed on the PCB as a counterbalance to the conductive traces to better maintain the flatness of the PCB. These might be, for example, nonconductive traces or additional conductive traces that have no electrical connections.

Figure 14:
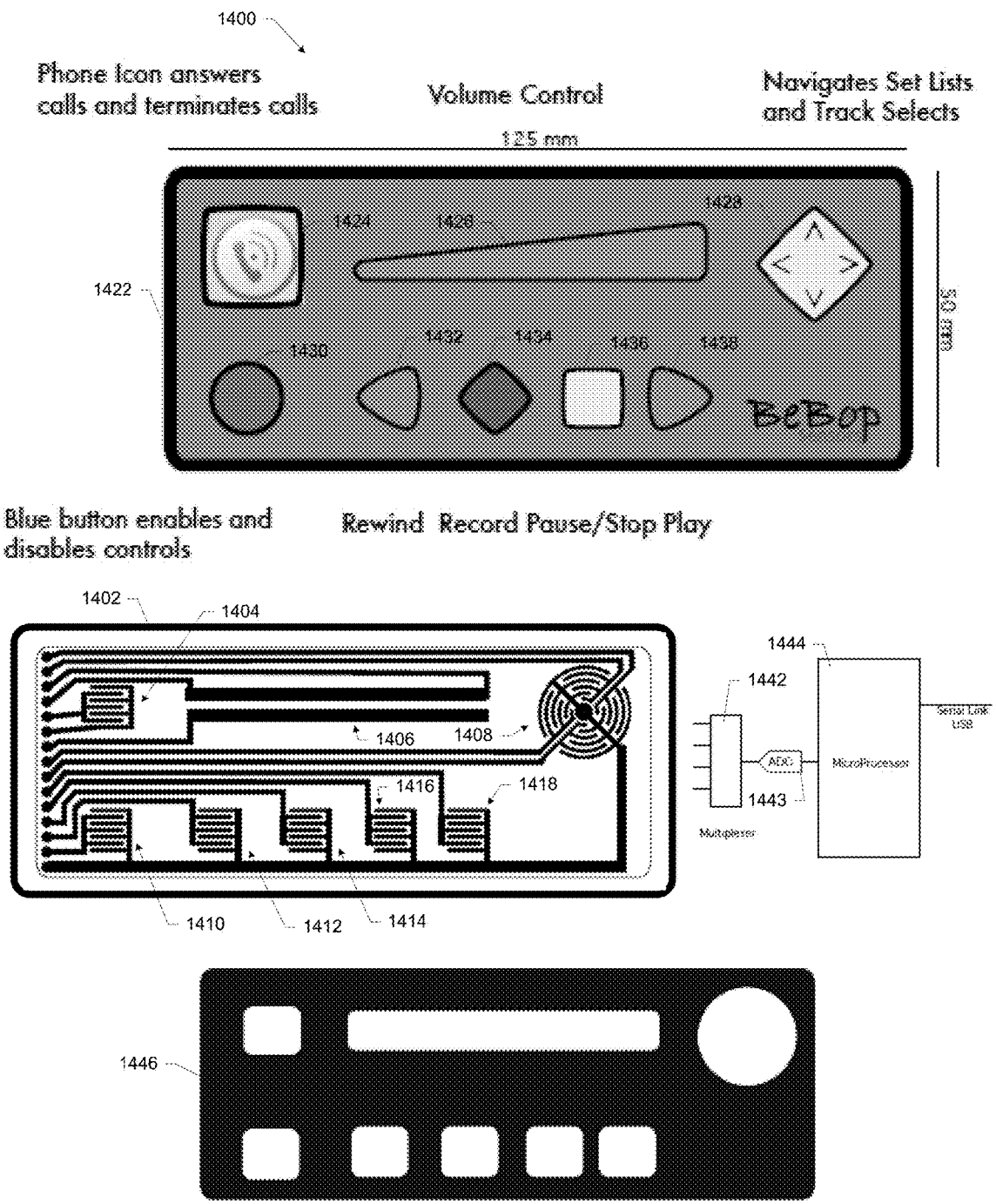
FIG. 14 illustrates a controller that employs a variety of sensor configurations.

It will be appreciated that sensors and sensor arrays designed as described in this disclosure may be employed in a very broad and diverse range of applications in addition to those described. One example of such an application is a controller 1400 for a smart phone or a digital media player as shown in FIG. 14. Controller 1400 may be implemented with an underlying piezoresistive substrate 1402 with conductive traces patterns 1404-1418 formed directly on or otherwise integrated with the substrate to implement sensors that provide different types of controls. The trace patterns are aligned with a particular icon representing the control on an overlying substrate 1422 with which a user interacts (i.e., icons 1424-1438). Alternatively, trace patterns 1404-1418 may be formed on the opposite side of the same substrate from icons 1424-1438. The substrate(s) from which controller 1400 is constructed may be a piezoresistive fabric that may be incorporated, for example, in articles of clothing, e.g., in the sleeve of a shirt or jacket.

As described elsewhere herein, when pressure is applied to one of the controls, a resulting signal may be digitized and mapped by associated processing circuitry (e.g., multiplexer 1442, A-D converter 1443, and processor 1444) to a control function associated with a connected device, e.g., the smart phone or media player (not shown) via, for example, a USB or Bluetooth connection. As will be appreciated, similar conversion and processing circuitry may be employed with any of the sensor configurations described herein.

In the depicted implementation, trace pattern 1404 corresponds to icon 1424 and implements a button control that allows the user to answer or terminate calls on his smart phone. Trace pattern 1406 corresponds to icon 1426 and implements a slider (such as the one described above with reference to FIG. 7) for volume control of, for example, a media player. Trace pattern 1408 corresponds to icon 1428 and implements a four-quadrant sensor that may be used for navigation of, for example, set lists, track queues, etc. Trace pattern 1410 corresponds to icon 1430 and implements an enable/disable control by which controller 1400 may be enabled and disabled. Trace patterns 1412-1418 correspond to icons 1432-1438, respectively, and implement various media player controls such as, for example, play, pause, stop, record, skip forward, skip back, forward and reverse high-speed playback, etc. As will be appreciated, this is merely one example of a wide variety of controllers and control functions that may be implemented in this manner.

According to a particular implementation, an insulating layer 1446 may be printed or deposited on piezoresistive substrate 1402 before any of trace patterns 1404-1418. As can be seen, openings in insulating layer 1446 line up with the portions of the trace patterns intended to implement the corresponding control functions. These portions of the trace patterns are therefore printed or deposited directly on the underlying piezoresistive substrate. By contrast, the conductive traces that connect these portions of the trace patterns to the edge of the piezoresistive substrate for routing to the processing circuitry are printed or deposited on insulating layer 1446. This will significantly reduce crosstalk noise between these conductors relative to an approach in which they are also printed on the piezoresistive substrate.

Two-dimensional sensor arrays incorporating piezoresistive materials are described in this disclosure. Specific implementations are described below including the best modes contemplated. Examples of these implementations are illustrated in the accompanying drawings. However, the scope of this disclosure is not limited to the described implementations. Rather, this disclosure is intended to cover alternatives, modifications, and equivalents of these implementations. In the following description, specific details are set forth in order to provide a thorough understanding of the described implementations. Some implementations may be practiced without some or all of these specific details. In addition, well known features may not have been described in detail to promote clarity.

As discussed above, piezoresistive materials include any of a class of materials that exhibits a change in electrical resistance in response to mechanical force or pressure applied to the material. A signal representative of the magnitude of the applied force is generated based on the change in resistance. This signal is captured via conductive traces (e.g., as a voltage or a current with the piezoresistive material as part of a divider circuit), digitized (e.g., via an analog-to-digital converter), processed (e.g., by an associated processor or controller or suitable control circuitry), and mapped (e.g., by the associated processor, controller, control circuitry, or a connected computing system) to a control function that may be used in conjunction with virtually any type of process, device, or system.

Figure 15A:
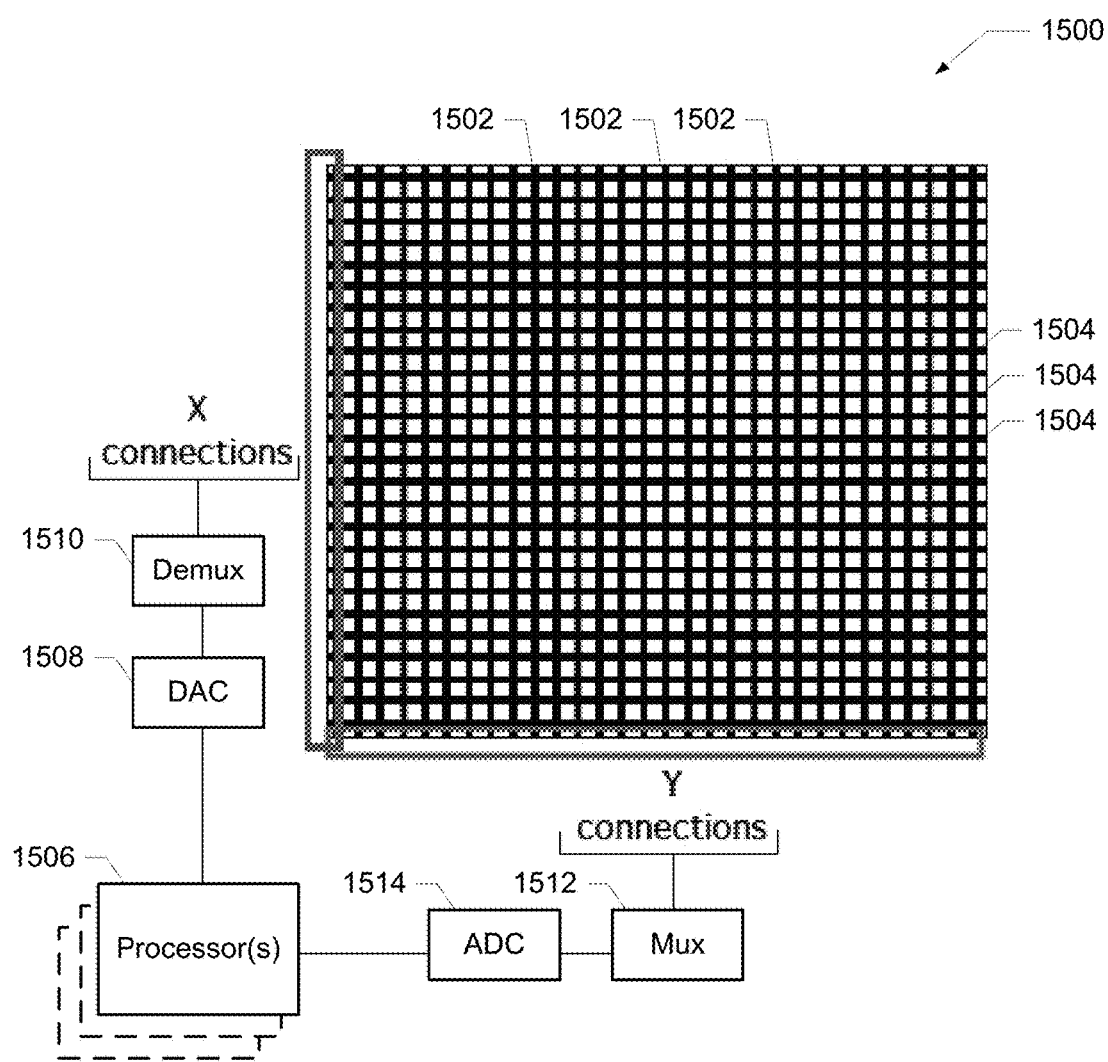

FIG. 15A shows an example of a two-dimensional sensor array 1500 that includes a set of substantially parallel conductive traces 1502 oriented in one direction, and another set of substantially parallel conductive traces 1504 oriented at about 90 degrees to the first set of traces. Traces 1502 and traces 1504 are electrically connected via a piezoresistive material (not shown for clarity). The traces and the piezoresistive material may be positioned relative to each other in a number of ways. For example, the piezoresistive material may be a fabric or other flexible substrate and the traces may be formed on the piezoresistive material on opposite sides of the material. In another example, the piezoresistive material might be sandwiched between two substrates on which the traces are formed or of which they are a part. In yet another example, both arrays of traces may be on the same side of a piezoresistive substrate (formed either on the piezoresistive material or separately from the piezoresistive material on or as part of an adjacent substrate) with insulation between the traces where they intersect or coincide. Additional substrates that are adjacent the piezoresistive material may also be fabric or other flexible materials. In implementations in which traces are formed on or part of one or more such substrates, the piezoresistive material may be coupled (e.g., laminated) to the additional substrate(s) to form a multilayer structure. Other suitable variations are within the scope of this disclosure.

By sequentially driving the traces of one set (e.g., using processor(s) 1506, digital-to-analog converter 1508, and demultiplexer 1510), and sequentially scanning the traces of the other (e.g., using multiplexer 1512, analog-to-digital converter 1514, and processor(s) 1506), both the position and force of a touch event on the array can be detected. And because of the sequential selection and activation of the traces, such a configuration is capable of detecting multiple touch events substantially simultaneously. As will be understood, the applications for such sensor arrays are virtually limitless.

FIG. 15B shows another example of a two-dimensional sensor array 1550 that includes a set of substantially parallel conductive traces 1552 oriented in one direction, and another set of substantially parallel conductive traces 1554 oriented at about 90 degrees to the first set of traces. Sensor trace patterns 1556 are provided near the intersections of the horizontal and vertical traces; each pattern including a trace 1558 connected to one of the vertical traces 1552, and a trace 1560 connected to one of the horizontal traces 1554. The depicted example employs a cruciform shape for trace 1560 and a clover shape for trace 1558 that provides a significant area in which the two conductive traces of the pattern are in close proximity to each other. As will be appreciated, the shapes of traces 1558 and 1560 and the distance(s) between them may be controlled to achieve a desired sensitivity (dynamic range) for a given application. Examples of other traces patterns that may be suitable for particular applications (e.g., 1556-1 through 1556-4) are shown. A variety of other configurations are within the scope of this disclosure.

Traces 1552 and 1558 are electrically connected with traces 1554 and 1560 via a piezoresistive material (not shown for clarity). According to some implementations of sensor array 150, the arrays of parallel traces and the trace patterns are formed on one side of the piezoresistive material (either on the piezoresistive material or on a substrate that is adjacent the piezoresistive material). In such implementations insulating material 1562 is provided at the intersections of the parallel traces 1552 and 1554 to insulate these traces from each other. However, it should be understood that, as with sensor array 1500, implementations are contemplated in which the traces of the respective arrays are disposed on opposite sides of intervening piezoresistive material (e.g., traces 1552 and 1558 on one side of the material and traces 1554 and 1560 on the other).

Sensor array 1550 has associated circuitry 1564 (which may be similar to the circuitry shown in FIG. 15A) configured to apply drive signals to one set of conductive traces and to receive detection signals from the other. As discussed above with reference to sensor array 1500, sequential selection and activation of the traces by circuitry 1564 enables detection of the position and force of a touch event on the array, as well as the detection of multiple simultaneous touch events.

According to some implementations, the signal quality for touch events on two-dimensional arrays such as arrays 1500 and 1550 may be improved by connecting other traces in the array to a known potential (e.g., ground) when a signal from a particular trace is being read (rather than leaving them floating). This may reduce contributions from touch events associated with the other vertical traces.

According to a particular class of implementations, conductive traces are printed, screened, deposited, or otherwise formed onto flexible piezoresistive material. As discussed above, this allows for the creation of a sensor array that fits any arbitrary shape or volume. The piezoresistive material may be any of a variety of woven and non-woven fabrics having piezoresistive properties. Implementations are also contemplated in which the piezoresistive material may be any of a variety of flexible materials (e.g., rubber, or a stretchable fabric such as spandex or open mesh fabrics) having piezoresistive properties. The conductive traces may be arranged in a variety of ways depending on the shape or volume to which the array is designed to conform. For example, the rectilinear configurations shown in FIGS. 15A and 15B may be suitable for substantially flat implementations, while varying degrees of curvature of the traces and/or shaping of the overall shape of the array may be desired for arrays conforming to other types of surfaces or shapes. According to some implementations, only portions of an array might be used to enable the folding or rolling up of the array into a desired form factor, e.g., if the upper right hand corner of array 1550 is removed, the remainder of the array could be rolled into a conical shape. Other such Euclidean transformations to achieve different shapes and form factors are within the scope of this disclosure.

The traces may be formed using any of a variety of conductive inks or paints. Implementations are also contemplated in which the conductive traces are formed using any flexible conductive material that may be formed on the flexible piezoresistive material. It should therefore be understood that, while specific implementations are described with reference to specific materials and techniques, the scope of this disclosure is not so limited.

Both one-sided and two-side implementations are contemplated, e.g., conductive traces can be printed on one or both sides of the piezoresistive material. As will be understood, two-sided implementations may require some mechanism for connecting conductive traces on one side of the piezoresistive material to those on the other side. Some implementations may use vias in which conductive ink or paint is flowed through the via to establish the connection. Alternatively, metal vias or rivets may make connections through the piezoresistive material.

Both single and double-sided implementations may use insulating materials formed over the piezoresistive material and/or the conductive traces. This allows for the stacking or layering of conductive traces and signal lines, e.g., to allow the routing of signal line to isolated structures in a manner analogous to the different layers of a PCB.

Routing of signals on and off the piezoresistive material may be achieved in a variety of ways. A particular class of implementations uses elastomeric connectors (e.g., ZEBRA® connectors) which alternate conductive and non-conductive rubber at a density typically an order of magnitude greater than the width of the conductive traces to which they connect (e.g., at the edge of the piezoresistive material). Alternatively, a circuit board made of a flexible material (e.g., Kapton), or a bundle of conductors may be riveted to the piezoresistive material. The use of rivets may also provide mechanical reinforcement to the connection.

Matching conductive traces or pads on both the piezoresistive material and the flexible circuit board can be made to face each. A layer of conductive adhesive (e.g., a conductive epoxy such as Masterbond EP79 from Masterbond, Inc. of Hackensack, N.J.) can be applied to one of the surfaces and then mated to the other surface. The conductive traces or pads can also be held together with additional mechanical elements such as a plastic sonic weld or rivets. If conductive rivets are used to make the electrical connections to the conductive traces of the piezoresistive material, the conductive adhesive may not be required. Conductive threads may also be used to connect the conductive traces of the piezoresistive material to an external assembly.

According to a some implementations, the piezoresistive material is a pressure sensitive fabric manufactured by Eeonyx, Inc., of Pinole, Calif. The fabric includes conductive particles that are polymerized to keep them suspended in the fabric. The base material is a polyester felt selected for uniformity in density and thickness as this promotes greater uniformity in conductivity of the finished piezoresistive fabric. That is, the mechanical uniformity of the base material results in a more even distribution of conductive particles when a slurry containing the conductive particles is introduced. The fabric may be woven. Alternatively, the fabric may be non-woven such as, for example, a calendared fabric e.g., fibers, bonded together by chemical, mechanical, heat or solvent treatment. Calendared material may present a smoother outer surface which promotes more accurate screening of conductive inks than a non-calendared material.

The conductive particles in the fabric may be any of a wide variety of materials including, for example, silver, copper, gold, aluminum, carbon, etc. Some implementations may employ carbon graphenes that are formed to grip the fabric. Piezoresistive materials may be fabricated using techniques described in U.S. Pat. No. 7,468,332 for Electroconductive Woven and Non-Woven Fabric issued on Dec. 23, 2008, the entire disclosure of which is incorporated herein by reference for all purposes. However, it should again be noted that any flexible material that exhibits a change in resistance or conductivity when pressure is applied to the material and on which conductive traces may be printed, screened, deposited, or otherwise formed will be suitable for implementation of sensor arrays as described herein.

According to a particular class of implementations, conductive traces having varying levels of conductivity are formed on the piezoresistive material using conductive silicone-based inks manufactured by, for example, E.I. du Pont de Nemours and Company (DuPont) of Wilmington, Del., and/or Creative Materials of Ayer, Mass. An example of a conductive ink suitable for implementing highly conductive traces for use with various implementations is product number 125-19 from Creative Materials, a flexible, high temperature, electrically conductive ink. Examples of conductive inks for implementing lower conductivity traces for use with various implementations are product numbers 7102 and 7105 from DuPont, both carbon conductive compositions. Examples of dielectric materials suitable for implementing insulators for use with various implementations are product numbers 5018 and 5036 from DuPont, a UV curable dielectric and an encapsulant, respectively. These inks are flexible and durable and can handle creasing, washing, etc. The degree of conductivity for different traces and applications is controlled by the amount or concentration of conductive particles (e.g., silver, copper, aluminum, carbon, etc.) suspended in the silicone. These inks can be screen printed or printed from an inkjet printer. Another class of implementations uses conductive paints (e.g., carbon particles mixed with paint) such as those that are commonly used for EMI shielding and ESD protection.

The dynamic range of a two-dimensional sensor array implemented as described herein may be manipulated through the use of a variety of mechanical structures that may be included in or on any of the layers, substrates, or components of the array. Such structures may be flexible (e.g., silicone) components or features, the characteristics of which (e.g., shape, size, height, flexibility, number, placement, etc.) may be manipulated to provide resistance to applied physical forces such that a desired dynamic range of the sensors is achieved. Some examples of such structures are described below with reference to FIG. 18. A wide variety of other structures and components suitable for achieving a desired sensitivity or dynamic range are within the scope of the disclosure.

As will be understood by those of skill in the art, a variety of techniques may be employed to acquire data from sensors constructed as described herein. Some of these techniques may involve a simple measurement of a change in resistance (as determined from a voltage or current measurement) between two coinciding conductive traces having the same or similar conductivity. However, for sensors having arrays that include many conductive traces, this may require an unacceptable number of signal lines to route signals both to and from the sensor array. For example, for the implementation of FIG. 15A having X traces 1504 and Y traces 1502, the number of signal lines to the associated circuitry would be X+Y. As will be understood, for very large arrays this may become difficult to implement. Therefore, according to a particular class of implementations, conductive traces formed on piezoresistive material and having different levels of conductivity are driven and interrogated with signal patterns that reduce the number of signal lines required to achieve sensor configurations that are sensitive to location, pressure, direction, and velocity of applied force.

Figure 16:
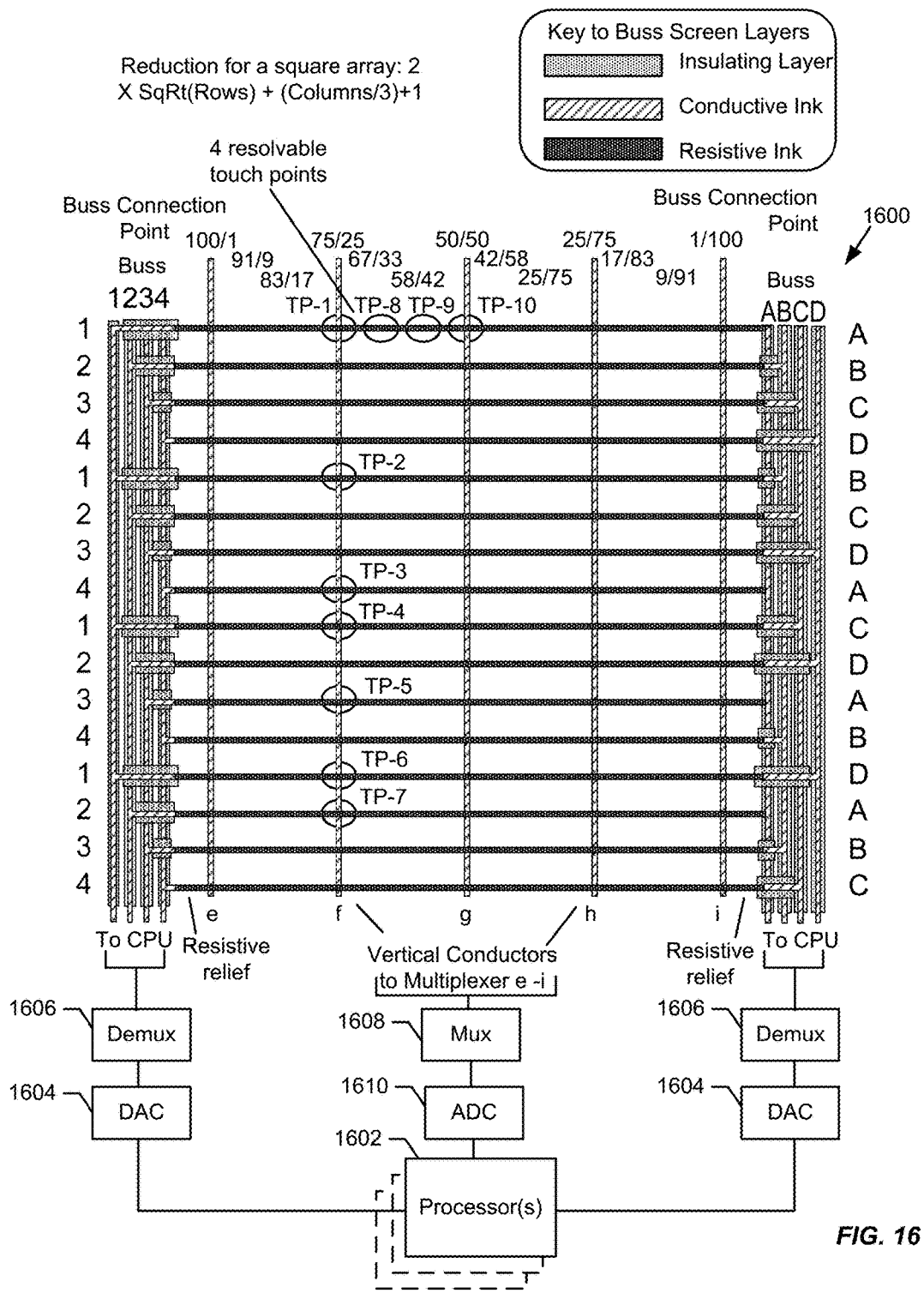
FIG. 16 is another simplified representation of a two-dimensional sensor array.

FIG. 16 illustrates a particular implementation of a two-dimensional sensor array 1600 that includes an array of parallel traces that are highly conductive (e.g., near zero resistance) oriented in a first direction (vertically in the figure), and an array of parallel traces that are less conductive (e.g., about 500 to 1000 ohms each from end to end) oriented in a second direction (horizontally in the figure). Electrical connections between the traces are made via a piezoresistive material (not shown for clarity). As with the implementation described above with reference to FIGS. 15A and 15B, the traces and the piezoresistive material may be positioned relative to each other in a variety of ways. Further, the conductive traces may be configured to conform to a particular surface or volume. So, although the implementation of FIG. 16 illustrates a rectilinear array of traces that are formed on opposite sides of a piezoresistive substrate, the scope of this disclosure is not so limited.

Drive signals generated by processor(s) 1602 are transmitted to the horizontal traces via digital-to-analog converter 1604, de-multiplexer 1606, and busses 1-4 and A-D. Each horizontal trace is designated by the pair of busses to which it is connected, i.e., the top horizontal trace in FIG. 16 is trace 1A, the next trace down is trace 2B, and so on. No two horizontal traces are connected to the same pair of busses. Signals are received by processor(s) 1602 from vertical traces e-i via multiplexer 1608, and analog-to-digital converter 1610. The resolution of the array along the vertical axis is determined by the number and spacing of the horizontal traces. That is, the location of a touch event along this axis is determined by the location of the horizontal trace for which it detected. However, as will be discussed, the resolution along the horizontal axis is greater than what is possible with the depicted number and spacing of the vertical traces using conventional techniques.

In addition, as will be appreciated from the figure, the number of signal lines that must be routed to and from array 1600 is many fewer than what is required for conventional arrays of comparable resolution. That is, a two-dimensional array typically has one signal line for each horizontal and each vertical channel, e.g., requiring X+Y signal lines to be routed off the array. By contrast, in the example illustrated in FIG. 16, array 1600 requires only 8 signal lines for 16 horizontal traces, and only 5 signal lines for vertical traces that provide a resolution along the horizontal axis that would require many more vertical traces in a conventional array. This may be achieved as follows.

In operation, each horizontal trace is energized in succession by simultaneously driving the opposing ends of the trace with primary detection signals S1 and S2 (shown in FIG. 17). While each horizontal trace is energized, signals are read from the vertical traces in succession. The force of a touch event on the piezoresistive material reduces the resistance between intersecting traces near the touch point which, depending on its location along the horizontal trace, results in different contributions from signals S1 and S2 measured in a mixed signal on the highly conductive vertical trace. The overall amplitude of the mixed signal represents the magnitude of the force. By determining the relative contributions of S1 and S2 to the mixed signal a horizontal location for the touch point may be determined.

According to a particular implementation and as illustrated in FIG. 17, primary detection signals S1 and S2 are different pulse trains of the same amplitude but with different duty cycles (e.g., S1 at 1 kHz with a 50% duty cycle, and S2 at 500 Hz with a 75% duty cycle), with the phases of the two pulse trains synchronized as shown. Location information may be derived from the mixed signal measured on the vertical conductive trace as follows. The signal on the vertical trace is sampled by A/D converter 1610 (e.g., oversampled by a factor of two or more relative to the frequency of the inputs). For processor(s) 1602, an inexpensive, general-purpose processor may be employed that can read up to 40 signals with up to 10-bits of resolution, and take 500K samples per second. The same general processor may drive the conductive traces. As will be appreciated, having the same processor generate the signals and perform the A/D conversion simplifies timing of samples to coincide with changes of the drive states. It also reduces the overall space or volume taken up by these components and keeps costs down. Thus, large arrays may be constructed relatively inexpensively. However, it should also be understood that implementations are contemplated in which different processors may perform these functions. More generally and as will be understood by those of skill in the art, a wide variety of suitable processors, controllers, computing devices, logic devices and other suitable circuitry may be adapted to control the sensors and sensor arrays described herein. Therefore, reference to specific circuitry or devices should not be used to limit the scope of this disclosure.

Figure 18:
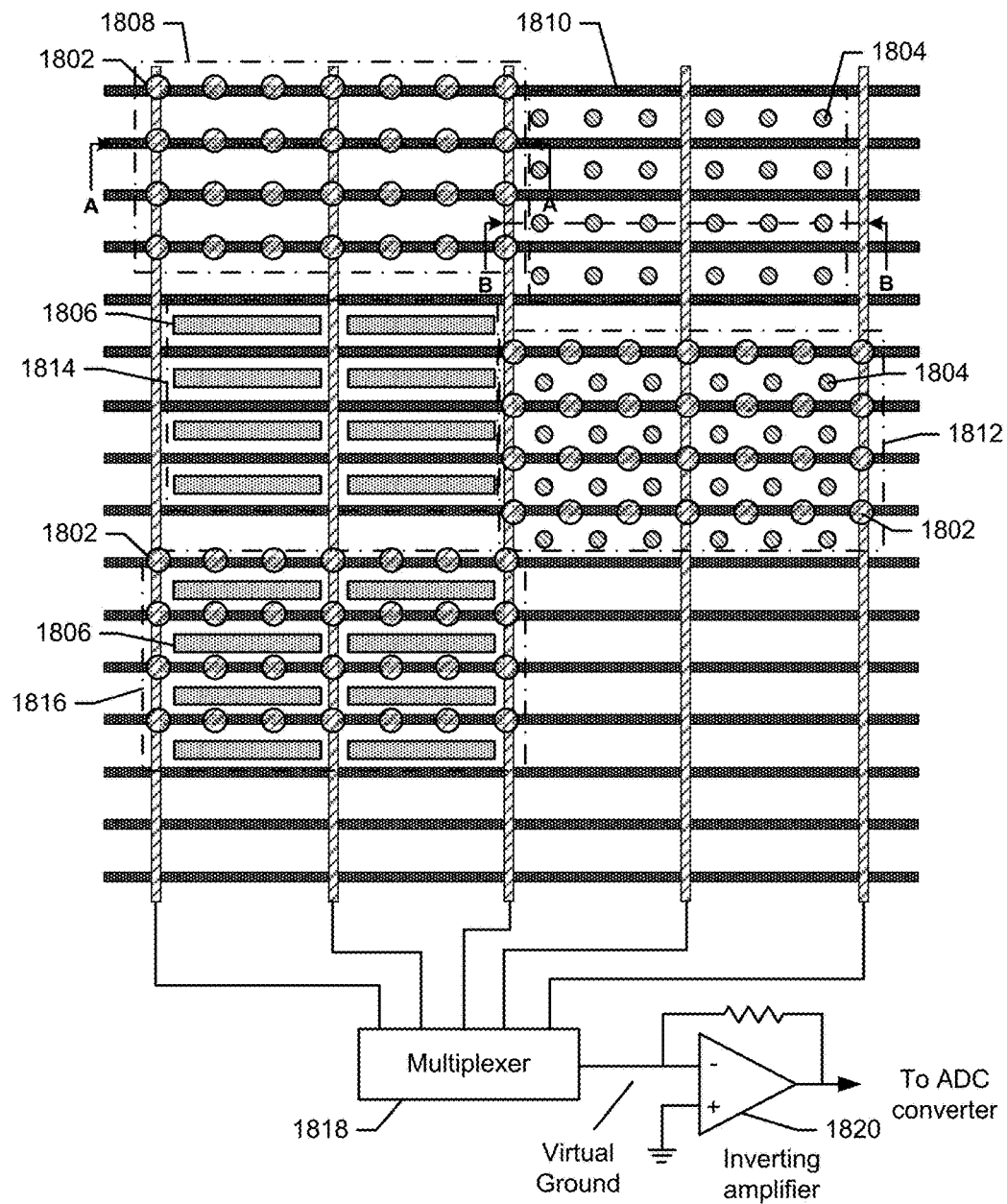
FIG. 18 illustrates examples of a variety of mechanical features for use with two-dimensional sensor array.

According to some implementations and as shown in FIG. 18, the vertical traces go through a multiplexer 1818 and into an inverting operational amplifier 1820 that represents a virtual ground reference. As a result, the signal (e.g., a current) measured on any one of the vertical traces will experience the lowest impedance to a ground reference and be accurately representative of any nearby touch events in that contributions from more remote touch events on the array have a much higher resistive path and are dominated by the contributions from local events.

The processor evaluates specific amplitudes at specific times that are correlated with the values of signals S1 and S2 at those times. The relative contribution from each signal is determined by selecting closely-spaced samples of the mixed signal at times when the respective signals are each known to have a particular value or characteristic, e.g., full amplitude. The ratio of those two measurements represents the relative contributions of each signal to the mixed signal that, in turn, can be mapped to a location between the end points of the trace. Examples of ratios of the contributions of signals S1 and S2 representing different touch points along the horizontal axis are shown in FIG. 16, e.g., 75/25 corresponding to touch point TP-1, 67/33 corresponding to touch point TP-8, and so on. The pressure or force of the touch event can be determined by measuring peak values of the sampled mixed signal. Thus, both the locations and forces of touch events along the horizontal traces may be determined at touch points (TPs) that are between the vertical traces.

The resolution along the horizontal axis with which touch points may be detected may vary for different implementations. According to some implementations, the resolution may be very high with very precise locations determined. Alternatively and according to a particular class of implementations, the resolution may be designed to be appropriate for particular applications by quantizing the touch point locations. In such implementations, each horizontal trace may be thought of as a series of segments that each resolve to a particular touch point location along that trace. Quantization simplifies the detection of touch events by reducing the number of allowable locations to which the measured ratios map. For example, according to a particular implementation, there are only three allowable locations for each vertical trace along a particular horizontal trace; i.e., at the vertical trace itself and at locations immediately to its left and right. This may be understood with reference to FIG. 16.

In the depicted example, touch points TP-1, TP-8, TP-9 and TP-10 represent resolvable touch points along horizontal trace 1A. That is, any touch events falling along the segment of trace 1A within a particular one of the touch point ovals is resolved to the center of that segment. Put another way, the determined ratio of the relative contributions to the measured signal from primary detection signals S1 and S2 corresponds to a particular touch point if that ratio falls within a range of values associated with that touch point, e.g., TP-8 might correspond to values between 71/29 and 63/37. In this example then, each vertical trace may be used to detect 3 touch points along each horizontal trace, i.e., one at the trace and one on other side.

As will be appreciated, there may be situations in which the value derived from the signal on any one vertical trace may be ambiguous. For example, a single touch point at TP-8 might be indistinguishable from two simultaneous touch points at TP-1 and TP-9 if only the signal on vertical trace f is considered. Therefore, according to some implementations, the processor can distinguish between these two cases with reference to the values derived from signals on other vertical traces that are close in time. In this example, the signal on vertical trace g would be different for the single touch point case than it is for the two touch points due to the proximity of touch point TP-9.

Thus, the processor can use multiple values derived from adjacent vertical traces to disambiguate among various scenarios. More generally, implementations are contemplated in which the processor is configured to take into account multiple data points (separated in space and/or time) in order to accurately and reliably discriminate between scenarios that might otherwise be ambiguous. Another example of a technique that may be employed to disambiguate touch event scenarios involves connecting other vertical traces to a known potential (e.g., ground) when a particular vertical trace is being read (rather than leaving them floating). As discussed above with reference to the implementations of FIGS. 15A and 15B, this may reduce contributions from touch events associated with the other vertical traces. And as discussed in greater detail below, mechanical elements can be introduced that promote the quantization of touch point locations and may serve to further promote disambiguation.

According to some implementations, ambiguity may also be dealt with by generating multiple values for each vertical trace signal while a particular horizontal trace is energized. For example, horizontal trace 1A may be energized with signal S1 applied via buss 1 and signal S2 applied via buss A. Values are then successively generated by the processor for the signals received on vertical traces e-i. Horizontal trace 1A may then be energized by reversing the two primary detection signals (signal S1 on buss A and signal S2 on buss 1) and generating another set of values for the signals on traces e-i. This second set of values may be generated immediately following generation of the first set of values, or on a successive loop through all of the horizontal traces. As will be appreciated, this additional information may be used by the processor for discriminating between potentially ambiguous scenarios. For example, for a touch event at a particular touch point the same ratio of signal contribution should be determined regardless of the trace ends to which signals S1 and S2 are applied. The duplicative data may therefore be used to verify or validate the first data. Alternatively, the duplicate data values for a particular combination of horizontal and vertical trace could be averaged.

It should also be noted that the number and the size of touch points that can be resolved by a single vertical trace may vary. For example, the size of the touch points may correspond to the size of the average human fingertip. Alternatively, the size of the touch points may correspond to smaller instruments such as the tips of styluses or pointers. In addition, more than three touch points (e.g., 5 or 7) may be resolved by each vertical trace. It should also be noted that the number of touch points that may be resolved may also be constrained by the uniformity and consistency of the resistance of both the piezoresistive material and the horizontal traces, i.e., the greater the uniformity and/or consistency of these components, the greater the resolution that may be supported. On the other hand, because the values being generated are ratios (at least for touch event locations), as long as the resistance of a horizontal trace is relatively consistent along its length, there need not be a high level of consistency from one horizontal trace to the next.

As will be appreciated with reference to the foregoing, the techniques described herein may result in a significant reduction in signal lines required to bring signals to and from the array relative to conventional arrays of comparable resolution. However, as will also be appreciated, there may be scenarios in which multiple touch events occurring along the same vertical trace result in potentially ambiguous data. For example, touch events might occur simultaneously at touch points TP-1 and TP-2 in FIG. 16. When horizontal trace 1A is energized and the signal on vertical trace f is captured, there will be contributions to the captured signal from both touch events. That is, the touch event at touch point TP-1 will result in contributions from primary detection signals S1 and S2 in the mixed signal on trace f as described above. In addition, because buss 1 is also driven by signal S1, there will be a contribution to the signal on trace f from the touch event at TP-2 along horizontal trace 1B. Similarly, when trace 1B is selected for energizing, there will be contributions from both touch events in that data as well.

Therefore, according to some implementations, "ghost" detection signals are introduced in the array simultaneous with the primary detection signals. These signals allow the processor to account for any unwanted contributions from simultaneous events along the same vertical trace so that it can generate an accurate representation of any touch events along the primary horizontal trace being energized. The way in which this may be achieved may be understood with reference to FIGS. 16 and 17.

In this example, the primary horizontal trace being energized with primary detection signals S1 and S2 is trace 1A (i.e., the topmost trace in the figure), and the vertical trace for which a signal is being captured is trace f. Because buss 1 must be active for trace 1A to be energized, it is possible for unwanted contributions to the signal on trace f from signal S1 to come from touch events at TP-2, TP-4 and TP-6. Similarly, because buss A must also be active, unwanted contributions from signal S2 may result from touch events at TP-3, TP-5 and TP-7.

To account for the unwanted contribution from any touch event at TP-2, ghost detection signal S3 is introduced on buss B while trace 1A is energized. As discussed above, a touch event at touch point TP-2 may be represented by a ratio that represents the relative contributions of signals S1 and S3 at vertical trace f. Because this relationship is known, i.e., 75/25, and because the magnitude of the contribution from signal S3 is also known (because it is measured in isolation), the magnitude of the contribution from signal S1 due to a touch event at TP-2 may be determined and accounted for when calculating the values for a touch event at or near TP-1. Similarly, to account for the unwanted contribution from any touch event at TP-7, ghost detection signal S4 is introduced on buss 2 (not simultaneous with signal S3 on buss B because that would energize trace 2B).

In the depicted example, signal S3 is a 2 kHz signal with a 50% duty cycle, and signal S4 is a 3 kHz signal also with a 50% duty cycle. It will be understood that these are merely representative examples and that a wide range of alternatives may be employed for different applications; as long as the timing and amplitudes of the signals are such that the relative contributions of the various signals to a particular mixed signal can be determined as described.

To account for unwanted contributions for all possible touch events along vertical trace f while horizontal trace 1A is energized, ghost detection signals S3 and S4 are successively introduced for each touch point along vertical trace f for which such a contribution might occur. Thus, signal S3 is introduced successively to busses B, C and D to account for touch points TP-2, TP-4 and TP-6, respectively; and signal S4 is introduced successively to busses 4, 3 and 2 to account for touch points TP-3, TP-5 and TP-7, respectively. Ghost detection signals are introduced in a similar manner for each signal capture on vertical traces e-i. And this is done for each horizontal trace. Those of skill in the art will understand how to extrapolate from the foregoing discussion to account for all possible combinations of multiple touch events along any of the vertical traces.

As an alternative, instead of using two different ghost detection signals that are successively introduced, implementations are contemplated in which a sufficient number of unique ghost detection signals are simultaneously introduced. As another alternative, a single ghost detection signal can be introduced sequentially to all of the relevant busses (assuming the far side of the buss is grounded). In such implementations, the magnitude of the detected ghost signal would be stored while the ground and ghost detection signal are exchanged so that the ratio can then be computed.

Returning to the example in which horizontal trace 1A is energized, once all contributions to the signal on vertical trace f from other possible touch points along the vertical trace are identified, the unwanted contributions may be removed (e.g., subtracted) from the value being determined so that the horizontal position of any touch event along trace 1A (if any) may be determined from the resulting ratio as described above.

As each successive horizontal trace is energized, a pair of values is generated for each combination of an energized trace with each of the vertical traces. One value in the pair represents the relative contributions of the primary detection signals to the signal received on the vertical trace (e.g., expressed as a ratio), and the other the amplitude or magnitude of that signal (e.g., expressed as a value that is proportional to the force of the touch event; at least within the dynamic range of the piezoresistive material). In the example of array 1600 of FIG. 16, a single pass through the array would result in a data set having 80 pairs of such values, i.e., 5 pairs of values for each of 16 horizontal traces. Each of these pairs of values may or may not represent a touch event. The ways in which the data may be processed to determine whether or not a pair of values represents a meaningful event, i.e., a touch event, may vary considerably.

For example, in some implementations, a pair of values may be considered a touch event if the amplitude or magnitude value for the pair (e.g., a peak measurement of the received signal) exceeds a threshold. The threshold may be fixed or dynamic. For example, the threshold might be determined using an average of the amplitude measurements made across the array over a given time period (e.g., corresponding to a single pass through the array). If the amplitude value for a given pair of values exceeds the threshold, the pair of values is considered to represent a touch event, and the location of the touch event is determined with reference to the ratio value of the pair (e.g., mapped to a quantized touch point as discussed above).

Figure 20:
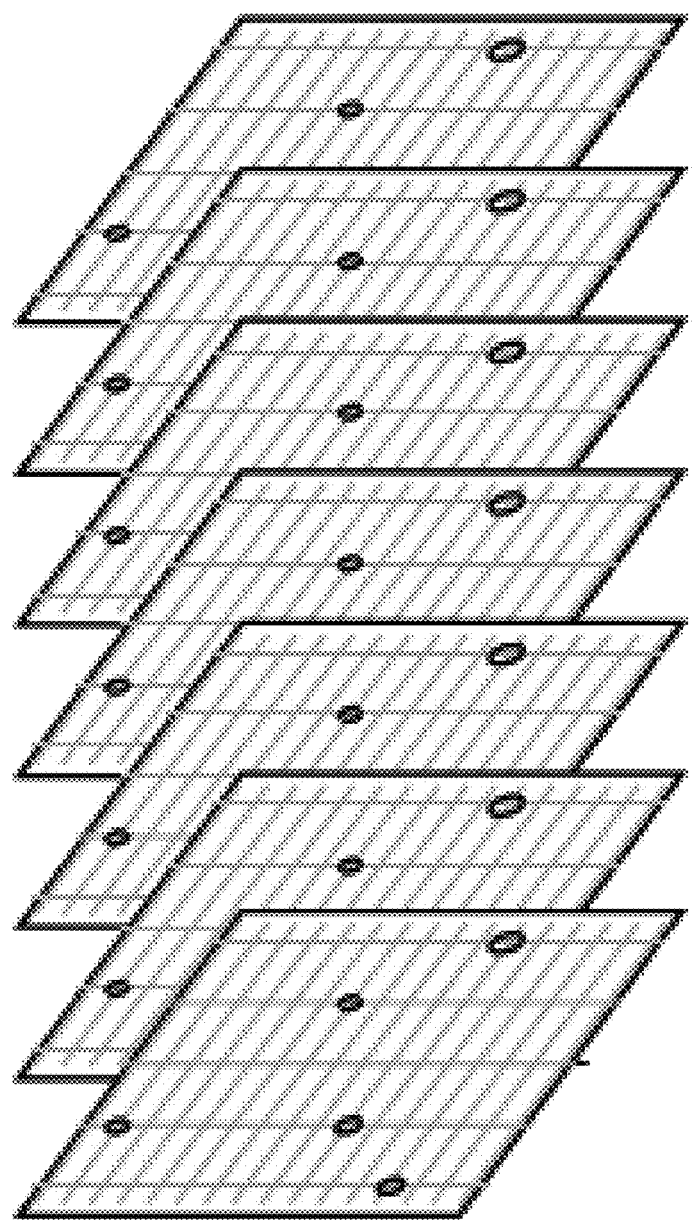
FIG. 20 provides a representation of data sets for a two-dimensional sensor array generated over time.

According to some implementations, the reliability with which touch events are detected may be enhanced by comparing the data sets generated by successive passes or "scans" through the array over time. A scan corresponds to energizing each of the horizontal traces once and reading signals from each of the vertical traces once for each horizontal trace. For a particular implementation of the example of FIG. 16, 5 signal reads (corresponding to vertical traces e-i) may occur for each of the 16 horizontal traces each scan. As discussed above, this results in 10 values for each horizontal trace; 5 ratios representing the relative contributions of signals S1 and S2 and 5 amplitudes representing the force of any touch events. Each set of 160 values may be thought of as a "frame" of data that may be compared to one or more previous and/or subsequent frames for the purpose of more accurately and reliably detecting touch events. This is illustrated in FIG. 20 in which 7 successive frames of data are represented.

According to some implementations, techniques developed for the processing of frames of video may be adapted to make detection of touch events more robust and reliable. For example, the primary and ghost detection signals described above with reference to FIG. 16 may be thought of like the RGB color components of a video frame with the strengths of the respective signals being analogous to the strengths of the RGB contributions. A frame could be saved each time the two primary detection signals are changed to a new resistive trace or reversed and for each iteration of the ghost detection signal states.

With such data methods of processing image data (e.g., for machine vision) would be applicable. Such methods often use versions of wavelet analysis to decompose a video frame. Because of the known constraints of our data (array size, time series) simplified forms of wavelet analysis may be suitable, making it possible to go readily from our input values to a simplified post analysis result.

According to some implementations, machine learning techniques may be employed that use of Markov chains or similar mechanisms to track changes over time. Markov modeling is regularly used to compare present states to previous states, providing specific classifications of the chain. Some implementations may use edge detection along with statistical approaches such as Bayesian methods to analyze data. Because of the highly constrained data sets that may be produced with some implementations, tools from the realm of video analysis lend themselves to robust solutions.

For additional information about signal processing techniques that may be adapted for use with implementations described herein please refer to (1) *Machine Learning for Multimodal Interaction: First International Workshop*; MLMI 2004, Martigny, Switzerland, Jun. 21-23, 2004, Revised Selected Papers (Google eBook); (2) *Automatic Video Object Segmentation Using Wavelet Transform and Moving Edge Detection*; Xiao-Yan Zhang and Rong-Chun Zhao; 2006 International Conference on Machine Learning and Cybernetics, 13-16 (August 2006); (3) *Human detection based on discrete Wavelet transform*; M. M. Deshpande, J. G. Rana, and M. M. Pawar; IET Chennai 3rd International on Sustainable Energy and Intelligent Systems (SEISCON 2012) (27-29 Dec. 2012); (4) *Wavelet-based Image Compression Using Support Vector Machine Learning and Encoding Techniques*; Rakib Ahmed; Proceedings of the 8th IASTED International Conference on Computer Graphics and Imaging (2005); (5) *Video Forensics in Temporal Domain using Machine Learning Techniques*; Sunil Jaiswal and Sunita Dhavale; I. J. Computer Network and Information Security (July 2013); (6) *Content Based Image Classification with Wavelet Relevance Vector Machines*; Arvind Tolambiya, S. Venkataraman, Prem K. Kalra; Soft Computing—A Fusion of Foundations, Methodologies and Applications—Special Issue on Pattern Recognition and Information Processing Using Neural Networks; Volume 14 Issue 2, (September 2009); and (7) *What to believe: Bayesian methods for data analysis*; John K. Kruschke; Trends in cognitive sciences, Volume 14, Issue 7 (July 2007). The entire disclosure of each of the foregoing is incorporated herein by reference for all purposes.

Depending on the application, and in particular for implementations in which traces are formed on a flexible piezoresistive substrate, some form of mechanical and/or environmental protection may be desirable. For example, thin silicone sheets could be laminated over one or both sides of the array.

According to various implementations, the quantization of touch points may be promoted by introducing mechanical structures in and around the array that effectively focus forces on the array toward the desired discrete locations. And as will be discussed, some of these structures may also be useful for optimizing an array for different ranges of applied force, providing mechanical support, promoting alignment of system components, and/or providing environmental protection. Examples of such structures will be discussed with reference to FIGS. 18 and 19.

FIG. 18 shows a section of a two-dimensional sensor array 1800 in which various mechanical features are shown in different regions of the array for the purpose of illustration. The depicted features include force focusing elements (e.g., bumps 1802), structural elements (e.g., posts 1804) and apertures (e.g., cutouts 1806). Bumps 1802 are illustrated by themselves in region 1808. Posts 1804 are illustrated by themselves in region 1810. Bumps 1802 and posts 1804 are shown used together in region 1812. Cutouts 1806 are shown alone in region 1814 and in combination with bumps 1802 in region 1816. As will be appreciated, these regions are merely for illustration and that implementations are contemplated in which some or all of the features are used in various combinations.

Figure 19:
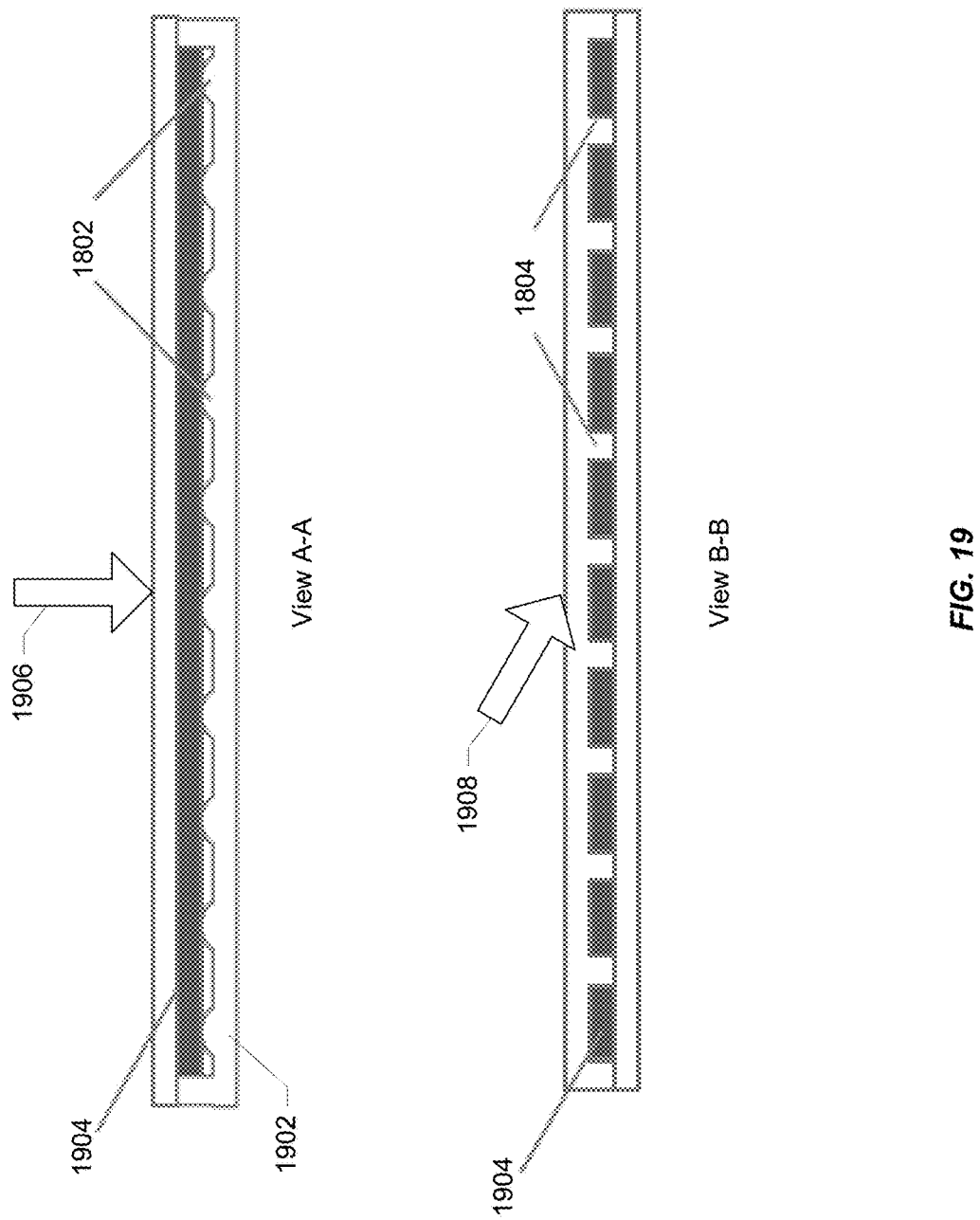
FIG. 19 includes cross-sectional views of two-dimensional sensor arrays.

According to a particular implementation and as illustrated in cross-sectional view A-A of FIG. 19, bumps 1802 may be convex features that are formed on or part of a molded silicone sheet 1902 that is aligned with and laminated to piezoresistive material 1904. In some cases, silicone sheet 1902 may form part of an enclosure that provides environmental protection to the enclosed components. In the depicted implementation, bumps 1802 are on the side of material away from the conductive traces and are aligned with the array's quantized touch points (e.g., TP-1 through TP-10 of FIG. 16), acting to focus force 1906 applied to the top of the array to those touch points. Alternatively, bumps 1802 may be formed on some other type of substrate (e.g., a rigid substrate like a printed circuit board). Bumps may also be formed in the piezoresistive material itself by shaping of the material at the desired locations. This may be accomplished by, for example, forming the bumps into the fabric when it is made or by embossing the features into the fabric. In another alternative, the bumps may be formed on a backing sheet to which the piezoresistive material is secured (e.g., laminated). Other variations apparent to those of skill in the art are within the scope of this disclosure. In addition, a wide variation in quantization and response (e.g., dynamic range) may be achieved by varying the size, height, spacing and flexibility of bumps 1802.

Posts 1804 extend through piezoresistive material 1904 as shown in cross section view B-B of FIG. 19 and may serve multiple purposes. For example, posts 1804 may serve to keep the array components aligned. This may be particularly important where posts 1804 are used in conjunction with bumps 1802 as shown in region 1812 of FIG. 18. Not only would such an arrangement serve to maintain alignment of bumps 1802 with the desired quantized touch points, posts 1804 may also serve to promote quantization by deflecting force laterally toward adjacent bumps 1802. In addition, the substrate from which posts 1804 extend may form part of an enclosure that provides environmental protection to the enclosed components.

According to some implementations, posts 1804 may not extend all of the way through piezoresistive material 1904 (i.e., being only secured to one of the substrates on either side of material 1904). This would mitigate the scenario in which a touch event occurs directly over a post. In such a scenario, if the post is rigid and extended all the way through the piezoresistive material, the touch event might not register. By contrast, if the post extended only part of the way through the piezoresistive material, a touch event over the post would result in some deflection that would transfer force to the piezoresistive material.

As an alternative and as depicted in FIG. 19, posts 1804 may extend all of the way through piezoresistive material 1904. In such implementations, posts 1804 may be constructed from a flexible material (e.g., silicone) so they compress with touch events. Posts 1804 might also be secured to both substrates on either side of the piezoresistive material. Such a configuration might be important, for example, in applications in which lateral shearing forces (e.g., force 1908) are expected on the surface of the array. In such applications, securing of the posts in this way would ensure that alignment is maintained in the presence of such shearing forces. Posts 1804 may also be tapered to promote some level of compression. More generally, the geometry (taper, thickness, etc.), flexibility, and spacing of posts 1804 may be controlled to achieve a desired array response.

Cutouts 1806 may be introduced in the piezoresistive material to promote isolation and inhibit cross-talk between conductive traces. This will improve the signal-to-noise ratio for the signals being read from the vertical traces and thereby improve overall system performance. And as will be appreciated, this may also serve to promote the quantization of touch point locations. And some implementations may take advantage of the absence of the piezoresistive material at the cutouts by including posts that are aligned with the cutouts. These may be like posts 1804 or may conform more closely to the shape of the cutout. For example, the posts could fill the cutout. As will be appreciated, such an approach would serve to provide mechanical structure, promote alignment, and/or promote a desired dynamic range.

As mentioned above, implementations enabled by this disclosure may be suitable for a broad range of applications. That is, two-dimensional sensor arrays as described herein may be useful in any context in which it is important or desirable to monitor the locations and magnitudes of forces on a surface at a point in time or over a period of time. In one example, such a two-dimensional array might be integrated in athletic footwear to monitor technique or track stress. In another example, a yoga mat might include such a two-dimensional array for the purpose of monitoring and/or teaching proper technique. In another example, the floor of an elder-care facility might include such arrays to indicate that a patient has fallen. In yet another example, an array might be integrated in the seat of an office chair to promote ergonomically sound posture. In still another example, a two-dimensional array might be incorporated in a mattress or pad for use in an infant's crib or bassinet. Such an array would be useful for monitoring an infant's sleeping position and to trigger an alarm when, for example, the sleeping position is determined to represent a high risk for sudden infant death syndrome (SIDS). As will be understood from the diversity of these examples, the potential applications of two-dimensional sensor arrays implemented as described herein are virtually limitless.

It will be understood by those skilled in the art that changes in the form and details of the implementations described herein may be made without departing from the scope of this disclosure. In addition, although various advantages and aspects have been described with reference to various implementations, the scope of this disclosure should not be limited by reference to such advantages and aspects. Rather, the scope of this disclosure should be determined with reference to the appended claims.

What is claimed is:

1. A sensor system, comprising:
   piezoresistive fabric;
   a flexible dielectric substrate having a plurality of conductive trace groups printed in conductive ink on a first side of the flexible dielectric substrate and a plurality of routing traces printed in conductive ink on a second side of the flexible dielectric substrate opposite the first side, the conductive trace groups and the piezoresistive fabric being in contact and forming a sensor array in which each of the conductive trace groups corresponds to a sensor in the sensor array, each of the conductive trace groups including two conductive traces, each of the conductive traces being electrically connected through the flexible dielectric substrate to a corresponding routing trace on the second side of the flexible dielectric substrate; and
   sensor circuitry configured to use the routing traces to energize the sensors and receive resulting sensor signals, the sensor circuitry also being configured to use the sensor signals to generate data representing locations and magnitudes of force resulting from objects in contact with a surface of the sensor system.

2. The sensor system of claim 1, wherein the sensor circuitry is further configured to generate successive frames of the data for the sensor array, and to compare the successive frames of the data to improve reliability of the data.

3. The sensor system of claim 1, wherein the two conductive traces of each conductive trace group comprise interdigitated extensions.

4. The sensor system of claim 1, wherein the two conductive traces of each conductive trace group comprise clover and cruciform shapes.

5. The sensor system of claim 1, wherein the piezoresistive fabric is a calendared material.

6. The sensor system of claim 5, wherein the piezoresistive material includes polymerized conductive particles.

7. The sensor system of claim 1, wherein one or more characteristics of the conductive trace groups are configured to achieve a particular dynamic range for the sensor system, the one or more characteristics including one or more of (1) shapes of the conductive traces of each conductive trace group, (2) distances between the conductive traces of each conductive trace group, or (3) conductivity of the conductive traces of each conductive trace group.

8. The sensor system of claim 1, further comprising one or more of (1) force focusing elements configured to focus the force on the surface of the sensor system toward one or more corresponding sensors of the sensor array, (2) structural elements configured to resist the force on the surface of the sensor system, or (3) cutouts in the piezoresistive fabric that promote physical and electrical isolation of adjacent sensors.

9. The sensor system of claim 1, wherein the conductive traces of each conductive trace group are electrically connected to the corresponding routing traces using conductive ink vias, conductive paint vias, metal vias, or metal rivets.

10. The sensor system of claim 1, wherein the piezoresistive fabric is a single substrate for all of the conductive trace groups.

11. The sensor system of claim 10, further comprising an insulating layer adjacent the piezoresistive fabric, the insulating layer having openings that line up with the conductive trace groups.

12. The sensor system of claim 1, wherein the piezoresistive fabric is multiple pieces, each piece of piezoresistive fabric corresponding to a different subset of the conductive trace groups.

13. The sensor system of claim 1, wherein the piezoresistive fabric is coupled to the flexible dielectric substrate.

14. The sensor system of claim 13, wherein the piezoresistive fabric is laminated to the flexible dielectric substrate.

15. The sensor system of claim 1, wherein the piezoresistive fabric is held at a distance from the conductive trace groups when pressure is not applied to the surface of the sensor system.

16. The sensor system of claim 1, further comprising an insulating material printed at locations at which two of the routing traces cross, the insulating material insulating the two routing traces from each other.

17. The sensor system of claim 1, wherein the sensor circuitry is configured to energize the sensors in a sequence and to receive the sensor signals in the sequence, and wherein the sensor circuitry is further configured to use the sensor signals to determine a speed of motion of a touch event relative to the surface of the sensor system, and a direction of motion of the touch event.

18. The sensor system of claim 1, wherein the sensor array is one of a linear array, a rectilinear array, a polar array, a hemispherical array, or an irregular two-dimensional array.

* * * * *